US012629320B2

(12) United States Patent
Hadad et al.

(10) Patent No.: US 12,629,320 B2
(45) Date of Patent: May 19, 2026

(54) CLOSED-SYSTEM DRUG-TRANSFER DEVICES FOR SOLID DOSAGE FORMS

(71) Applicant: RAMBAM MEDTECH LTD., Haifa (IL)

(72) Inventors: Salim Hadad, Haifa (IL); Zvi Lefel, Haifa (IL)

(73) Assignee: RAMBAM MEDTECH LTD., Haifa (IL)

( * ) Notice: Subject to any disclaimer, the term of this patent is extended or adjusted under 35 U.S.C. 154(b) by 1207 days.

(21) Appl. No.: 17/595,887

(22) PCT Filed: May 27, 2020

(86) PCT No.: PCT/IL2020/050582

§ 371 (c)(1),
(2) Date: Nov. 29, 2021

(87) PCT Pub. No.: WO2020/240554

PCT Pub. Date: Dec. 3, 2020

(65) Prior Publication Data

US 2022/0226196 A1     Jul. 21, 2022

Related U.S. Application Data

(60) Provisional application No. 62/882,716, filed on Aug. 5, 2019, provisional application No. 62/854,132, filed on May 29, 2019.

(51) Int. Cl.
*A61J 7/00*          (2006.01)
*A61J 15/00*         (2006.01)
(Continued)

(52) U.S. Cl.
CPC ........... *A61J 7/0007* (2013.01); *A61J 7/0053* (2013.01); *A61J 15/0026* (2013.01);
(Continued)

(58) Field of Classification Search
CPC .... A61J 7/0007; A61J 7/0053; A61J 15/0026; A61J 3/002; A61M 5/3135;
(Continued)

(56) References Cited

U.S. PATENT DOCUMENTS

| | | | | |
|---|---|---|---|---|
| 4,366,930 A | * | 1/1983 | Trombetti, Jr. ....... | A61J 7/0007 |
| | | | | 241/199.12 |
| 4,673,404 A | | 6/1987 | Gustavsson | |

(Continued)

FOREIGN PATENT DOCUMENTS

| | | |
|---|---|---|
| CN | 102921515 | 2/2013 |
| CN | 205948116 U | 2/2017 |

(Continued)

OTHER PUBLICATIONS

An International Search Report and a Written Opinion both dated Jul. 30, 2020, which issued during the prosecution of Applicant's PCT/IL2020/050582.

(Continued)

*Primary Examiner* — Chelsea E Stinson
*Assistant Examiner* — Nelson Louis Alvarado, Jr.
(74) *Attorney, Agent, or Firm* — Sughrue Mion, PLLC

(57)          ABSTRACT

A closed-system grinding syringe (10, 110) is provided for liquefying and delivering a solid dosage form (20), including a barrel (22), a fluid port (30) disposed on a bottom wall (28) of the barrel (22), and a plunger (32). A head (36) of the plunger (32) is insertable into and moveable within the barrel (22) such that (a) a portion of the barrel (22) defines a closed-system syringe chamber (46) between the bottom barrel wall (28) and a lower surface (64) of the plunger head (36), and (b) a plunger-head annular seal (42) forms a fluid-tight seal between an outer surface (44) of the plunger head (36) and a cylindrical inner surface (26) of the barrel (22). A solid-dosage-form support disc (60, 360) is disposed (Continued)

below a bottom plunger wall (38) so as to define a grinding compartment (62) between the lower surface (64) of the bottom plunger wall (38) and an upper surface (66) of the solid-dosage-form support disc (60, 360), and is shaped so as to define a plurality of holes (68, 368) through the solid-dosage-form support disc (60, 360).

23 Claims, 14 Drawing Sheets

(51) Int. Cl.
    *A61M 5/31*        (2006.01)
    *A61M 5/315*       (2006.01)
    *A61M 5/32*        (2006.01)
(52) U.S. Cl.
    CPC ...... *A61M 5/3135* (2013.01); *A61M 5/31513*
         (2013.01); *A61M 5/3295* (2013.01); *A61M*
         *2005/3128* (2013.01); *A61M 2005/3131*
         (2013.01); *A61M 2202/064* (2013.01)
(58) Field of Classification Search
    CPC ............ A61M 5/31513; A61M 5/3295; A61M
         2005/3128; A61M 2005/3131; A61M
         2202/064; A61M 5/1782; A61M 5/19
    See application file for complete search history.

(56)                    References Cited

U.S. PATENT DOCUMENTS

| | | | |
|---|---|---|---|
| 4,765,549 | A | 8/1988 | Sherman |
| 5,376,072 | A | 12/1994 | Klearman et al. |
| 5,472,421 | A * | 12/1995 | Klearman ........... A61M 5/3129 |
| | | | 604/82 |
| 5,827,262 | A | 10/1998 | Neftel et al. |
| 8,196,614 | B2 | 6/2012 | Kriheli |
| 9,610,222 | B2 | 4/2017 | Kriheli et al. |
| 9,656,022 | B1 | 5/2017 | Russo |
| 9,999,569 | B2 | 6/2018 | Kriheli |
| 2016/0354282 | A1 | 12/2016 | Macy, Jr. et al. |
| 2019/0000718 | A1 | 1/2019 | Kriheli et al. |
| 2019/0060170 | A1 | 2/2019 | Kriheli et al. |

FOREIGN PATENT DOCUMENTS

| | | |
|---|---|---|
| CN | 206910521 U | 1/2018 |
| CN | 208436090 | 1/2019 |
| CN | 109350833 A | 2/2019 |
| EP | 2135666 | 2/2012 |
| EP | 2549973 | 1/2015 |
| WO | 2009/095077 A1 | 8/2009 |
| WO | 2018/158768 | 9/2018 |

OTHER PUBLICATIONS

Albaut V et al., "Comparative Study Of the Different Closed System Transfer Devices Available in France for the Preparation of Injectable Immunotherapies," Sep. 21, 2021.
B. Braun, CSTD Performance Testing, Apr. 2019.
B. Braun, Cytotoxic Exposure & Healthcare Worker Risks, Apr. 2013.
B. Braun, OnGuard Materials of Construction List, May 25, 2020.
B. Braun, OnGuard® Closed System Transfer Device, (1) Oct. 2019.

B. Braun, OnGuard® Closed System Transfer Device, (2) Oct. 2019.
B. Braun, OnGuard® Cstd Designed for the Real World, Aug. 2019.
"ISOPP Standards for the Safe Handling of Cytotoxics," Journal of Oncology Pharmacy Practice. 2022;28(3_suppl):S1-S126. Apr. 2022; first published online: Mar. 31, 2022—Sections 1, 3, 6, an d7.
"Prepare your customers for USP <800>," www.repertoiremag.com, Nov. 2017.
Brown MJ et al., poster, "Head-to-head evaluation of closed-system transfer devices in a health-system oncology clinic," Novant Health, dated Feb. 2017.
Chemfort™ Instructions for Use (IFU), dated Oct. 2021.
Connor TH, "Safe Handling of Hazardous Drugs," NIOSH Science Blog, posted May 21, 2014.
Equashield Closed System Transfer Device Product Brochure downloaded May 6, 2019.
Equashield Closed System Transfer Device Technical Specification downloaded May 6, 2019.
Levin G et al. G3PC-011 "Closed system transfer device based on air filtration: the drug vapour challenge," 2020.
Levin G et al. G3PC-011 "Closed system transfer device based on air filtration: the drug vapour challenge," European Journal of Hospital Pharmacy Mar. 2020;27:A26-A27.
Simplivia™ Chemfort™—Compatibility with All Known Hazardous Drugs—Brochure, dated Nov. 3, 2022.
Simplivia™ Chemfort™—CSTD Guidelines—Brochure, dated Aug. 20, 2020.
Simplivia™ Chemfort™—Prevention of Hazardous Drug Vapor Release by the Chemfort™ Vial Adaptor, dated Jul. 21, 2022.
Simplivia™ Chemfort™—Safe Administration of Hazardous Drugs—Novel Approaches—Brochure, dated Dec. 13, 2021.
Simplivia™ Chemfort™ Syringe Adaptor Lock Brochure, dated Sep. 7, 2020.
Spencer SH et al., "Enteral tube administration of oral chemotherapy drugs," J Oncol Pharm Pract. Apr. 2020;26(3):703-717. Epub Jan. 19, 2020.
Tevadaptor® Closed System Components and Unique Sets Brochure, dated Jan. 8, 2018.
Vyas N et al., "Evaluation of a closed-system cytotoxic transfer device in a pharmaceutical isolator," J Oncol Pharm Pract. Feb. 2016;22(1):10-9. Epub Jul. 29, 2014.
Walker et al., "Integrity performance assessment of a Closed System Transfer Device syringe adaptor as a terminal closure for Luer-Lock syringes," medRxiiv preprint, Mar. 18, 2022 doi: https://doi.org/10.1101/2021.11.11.21266172.
White R, Bradnam V. Handbook of drug administration via enteral feeding tubes. Pharmaceutical Press; Mar. 11, 2015—Chapters 1, 6, 7, 8, and 11.
Wilkinson AS et al., "Integrity performance assessment of a closed system transfer device syringe adaptor lock as a terminal closure for Luer-Lock syringes," European Journal of Hospital Pharmacy Published Online First: Apr. 11, 2022. doi: 10.1136/ejhpharm-2021-003148.
U.S. Appl. No. 62/882,716, filed Aug. 5, 2019.
U.S. Appl. No. 62/854,132, filed May 29, 2019.
Chinese Office Action dated Jan. 31, 2024 in Application No. 202080054048.4.
An Office Action issued in Chinese Appl. No. CN 202080054048.4, dated Apr. 19, 2024.
Israeli Office Action dated Feb. 16, 2023 in Israeli Application No. 288517.
Extended European Search Report dated Jun. 13, 2023 in International Application No. 20812576.5.
Chinese Office Action dated May 18, 2023 in Chinese Application No. 202080054048.4.

* cited by examiner

FIG. 4K
FIG. 4L
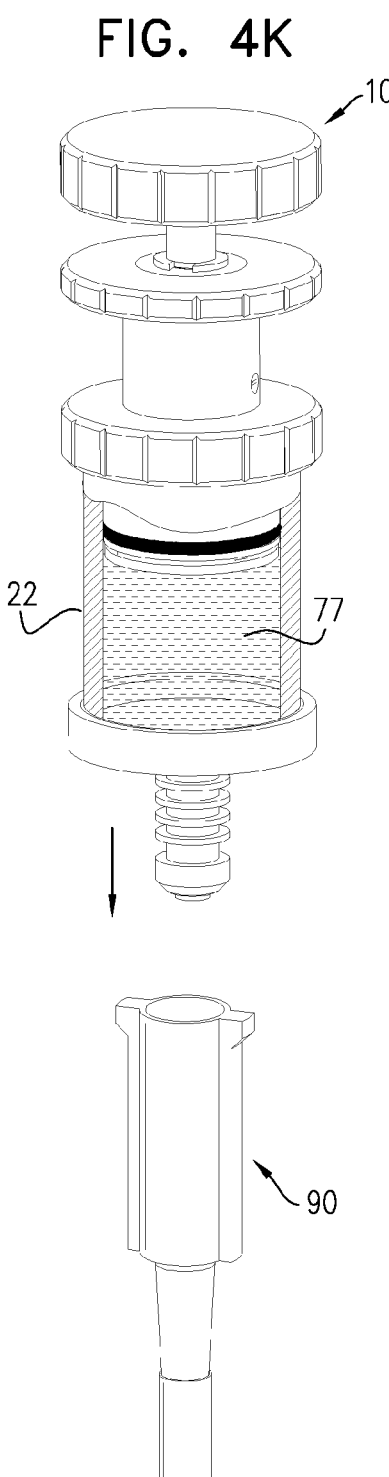
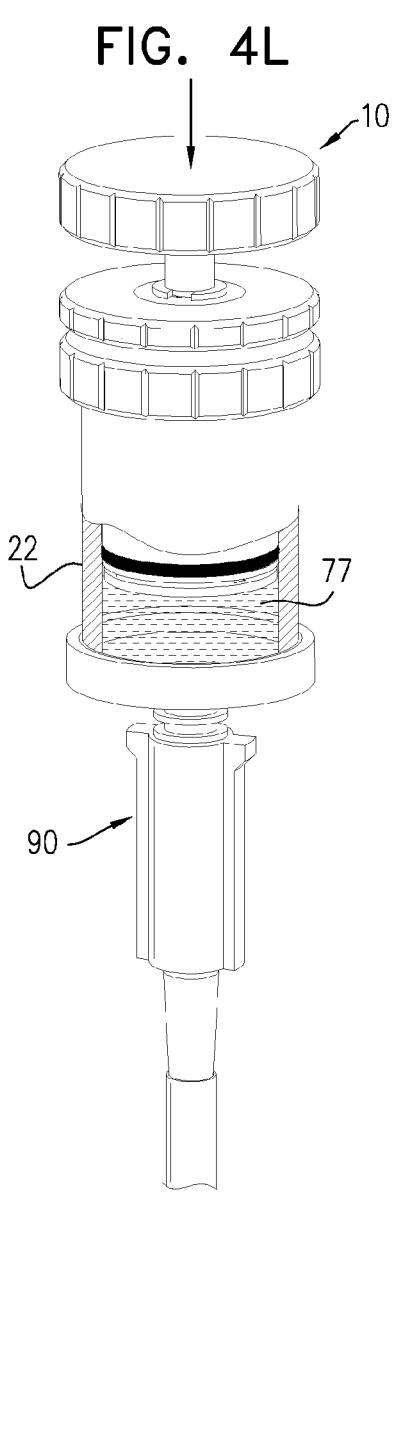

CLOSED-SYSTEM DRUG-TRANSFER DEVICES FOR SOLID DOSAGE FORMS

CROSS-REFERENCE TO RELATED APPLICATIONS

The present application is the U.S. national stage of International Application PCT/IL2020/050582, filed May 27, 2020, which claims priority from U.S. Provisional Application 62/854,132, filed May 29, 2019, and U.S. Provisional Application 62/882,716, filed Aug. 5, 2019, all of which are assigned to the assignee of the present application and incorporated herein by reference.

FIELD OF THE APPLICATION

The present invention relates generally to techniques for preparation of oral dosage forms.

BACKGROUND OF THE APPLICATION

A closed system drug transfer device (CSTD) is a drug transfer device that mechanically prohibits the transfer of environmental contaminants into the system and the escape of hazardous drug or vapor concentrations outside the system.

The U.S. National Institute for Occupational Safety and Health (NIOSH) has provided the following definitions of a closed system drug transfer device (CSTD):

"a drug-transfer device that mechanically prohibits the transfer of environmental contaminants into the system and the escape of hazardous drug or vapor concentrations outside the system" (NIOSH 2004).

"A drug containment device is one that is both airtight and leakproof."

Commercially available CSTDs for liquid dosage form products include the following: BD PhaSeal™ (Becton, Dickinson), Tevadaptor (Teva, Israel), Halo (Corvida, USA), ChemoClave (ICUmed, USA), Equashield II (Equashield, USA), and NeoShield® (JMS, Japan & USA).

In some common techniques for liquifying solid drug forms, the solid drug form is crushed and diluted in a vessel open to the environment, which may cause the work environment to be contaminated with carcinogenic or teratogenic substances, which might expose and endanger the medical staff to hazardous substances in the course of their duties as providers of medical care.

SUMMARY OF THE APPLICATION

Embodiments of the present invention provide a closed transfer system for solid oral dosage forms, which is configured to crush and liquefy solid oral drugs, such as solid cytotoxic drugs. The system performs the crushing and liquefaction under full sealing conditions, without allowing release of solid, liquid, or gaseous forms of the drug to the external environment, which might jeopardize the health of the attending healthcare workers. They system also mechanically prevents the transfer of environmental contaminants into the system.

Typically, the system is designed for single use, in order to obviate the need for complex cleaning of the system between operations, and to prevent cross-contamination between different drugs.

There is therefore provided, in accordance with an application of the present invention, apparatus including a closed-system grinding syringe for liquefying and delivering a solid dosage form, the closed-system grinding syringe including:

a barrel, which is shaped so as to define (a) a lateral wall shaped so as to define a cylindrical inner surface, (b) a top barrel opening, and (c) a bottom barrel wall;

a fluid port disposed on the bottom barrel wall;

a plunger, which includes a (a) plunger shaft; (b) a plunger head shaped so as to define a bottom plunger wall shaped so as to define a lower surface; and (c) a plunger-head annular seal, wherein the plunger head is insertable into and moveable within the barrel such that (a) a portion of the barrel defines a closed-system syringe chamber between the bottom barrel wall and the lower surface of the bottom plunger wall, and (b) the plunger-head annular seal forms a plunger-head fluid-tight seal between an outer surface of the plunger head and the cylindrical inner surface of the barrel;

a barrel cap, which is (a) configured to be attachable to the top barrel opening so as to form a barrel-cap fluid-tight seal with the top barrel opening, and (b) shaped so as to define a cap opening through the barrel cap, wherein the plunger shaft is slidably disposed through the cap opening so as to form a plunger-head fluid-tight seal between the plunger shaft and a perimeter of the cap opening;

a solid-dosage-form support disc, which (a) is disposed below the bottom plunger wall so as to define a grinding compartment between the lower surface of the bottom plunger wall and an upper surface of the solid-dosage-form support disc, and (b) is shaped so as to define a plurality of holes through the solid-dosage-form support disc; and a knob, wherein the closed-system grinding syringe is configured such that when (a) the solid dosage form is disposed in the grinding compartment, (b) the plunger head is inserted into the barrel, and (c) the closed-system grinding syringe is oriented upright, upon activation of the knob, the grinding compartment grinds the solid dosage form to a powder and at least 75% of the powder passes through the plurality of holes into a portion of the closed-system syringe chamber below the solid-dosage-form support disc.

For some applications, the closed-system grinding syringe is non-electrical and is configured such that when (a) the solid dosage form is disposed in the grinding compartment, (b) the plunger head is inserted into the barrel, and (c) the closed-system grinding syringe is oriented upright, upon mechanical activation of the knob, the grinding compartment grinds the solid dosage form.

For some applications, the lower surface of the bottom plunger wall is shaped so as to define grinding protrusions. For some of these applications, the holes of the solid-dosage-form support disc are aligned with the grinding protrusions, such that the grinding protrusions at least partially enter respective holes when the solid-dosage-form support disc moves closer to the lower surface of the bottom plunger wall. Alternatively or additionally, for some of these applications, the grinding protrusions are bottom-plunger-wall grinding protrusions, and the upper surface of the solid-dosage-form support disc is shaped so as to define support-disc grinding protrusions, which are not aligned with the bottom-plunger-wall grinding protrusions.

For some applications, the upper surface of the solid-dosage-form support disc is shaped so as to define support-disc grinding protrusions.

For some applications, the closed-system grinding syringe is configured such that the knob is activated by rotation thereof.

For some applications, the plunger shaft has a smaller average outer diameter than does the plunger head.

For some applications, the plunger is non-integral with the barrel, and separable from and coupleable to the barrel during normal use of the closed-system grinding syringe.

For some applications, the barrel cap is fixed to the plunger such that the plunger shaft is slidably disposed through the cap opening and the plunger is not separable from the barrel cap during the normal use of the closed-system grinding syringe.

For some applications, the plunger-head annular seal includes an O-ring.

For some applications, the fluid port includes a valve.

For some applications, the closed-system grinding syringe is configured to move the lower surface of the bottom plunger wall and the upper surface of the solid-dosage-form support disc closer to each other as the grinding compartment grinds the solid dosage form.

For some applications, the closed-system grinding syringe is configured such that the lower surface of the bottom plunger wall does not rotate while the lower surface of the bottom plunger wall and the upper surface of the solid-dosage-form support disc move closer to each other as the grinding compartment grinds the solid dosage form.

For some applications, the closed-system grinding syringe is configured to move the upper surface of the solid-dosage-form support disc with respect to the cylindrical inner surface of the barrel as the grinding compartment grinds the solid dosage form.

For some applications, the closed-system grinding syringe is configured such that the upper surface of the solid-dosage-form support disc does not rotate during upward movement of the dosage-form support disc with respect to the cylindrical inner surface of the barrel.

For some applications:

the closed-system grinding syringe further includes:

an axially-moveable shaft, which (a) is disposed partially within the plunger shaft, (b) forms a fluid-tight seal with an inner surface of the plunger shaft, (c) is connected to the solid-dosage-form support disc, (d) is rotationally-fixed with respect to the plunger shaft, and (e) is shaped so as to define an inner space having an internally-threaded wall; and an externally-threaded stem, which is (a) disposed partially within the plunger shaft, (b) axially fixed with respect to the plunger shaft, and (c) connected to the knob, and an external thread of the externally-threaded stem is mated with an internal thread of the internally-threaded wall, such that rotation of the externally-threaded stem in one rotational direction causes upward axial movement of the axially-moveable shaft with respect to the plunger shaft, which in turn moves the upper surface of the solid-dosage-form support disc upward with respect to the cylindrical inner surface of the barrel, causing the grinding compartment to grind the solid dosage form.

For some applications, the closed-system grinding syringe is shaped so as to define a liquid channel having (a) a first liquid-channel opening in fluid communication with the fluid port and (b) a second liquid-channel opening in fluid communication with the closed-system syringe chamber.

For some applications, the closed-system grinding syringe is shaped so as to define:

a liquid channel having (a) a first liquid-channel opening in fluid communication with the fluid port and (b) a second liquid-channel opening in fluid communication with the closed-system syringe chamber, and a gas channel having a first gas-channel opening in fluid communication with the fluid port.

For some applications:

the barrel is shaped so as to define an upper compartment between the barrel cap and the bottom plunger wall, when the barrel cap is attached to the top barrel opening, wherein the upper compartment is fluid-isolated from the closed-system syringe chamber and the external environment, the liquid channel has a second liquid-channel opening in fluid communication with the closed-system syringe chamber through the bottom barrel wall, and the gas channel has a second gas-channel opening in fluid communication with the upper compartment.

For some applications, at least a portion of the upper compartment is located within the plunger head.

For some applications, the liquid channel has a greater average inner diameter than does the gas channel.

For some applications, the grinding compartment is shaped so as to define one or more lateral openings for insertion of the solid dosage form into the grinding compartment.

For some applications, the one or more lateral openings are a single lateral opening that extends 360 degrees around the grinding compartment.

For some applications, the one or more lateral openings extend between 90 and 360 degrees around the grinding compartment.

For some applications, the fluid port is configured to mate with a tip of a syringe.

For some applications, the fluid port is shaped so as to define a female-taper fitting.

For some applications, the fluid port is configured to mate with a feeding tube.

For some applications, the feeding tube is selected from the group consisting of: a universal feeding tube, a percutaneous endoscopic gastrostomy (PEG) tube, a gastrostomy tube, and a nasogastric feeding tube.

For some applications, the apparatus further includes an adapter, which is configured to be sealingly coupled to the fluid port and to the feeding tube.

For some applications, the feeding tube is selected from the group consisting of: a universal feeding tube, a percutaneous endoscopic gastrostomy (PEG) tube, a gastrostomy tube, and a nasogastric feeding tube.

There is further provided, in accordance with an application of the present invention, a method of liquefying and delivering a solid dosage form, the method including:

providing a closed-system grinding syringe including:

a barrel, which is shaped so as to define (a) a lateral wall shaped so as to define a cylindrical inner surface, (b) a top barrel opening, and (c) a bottom barrel wall;

a fluid port disposed on the bottom barrel wall;

a plunger, which includes (a) a plunger shaft; (b) a plunger head shaped so as to define a bottom plunger wall shaped so as to define a lower surface; and (c) a plunger-head annular seal;

a barrel cap, which is shaped so as to define a cap opening through the barrel cap, wherein the plunger shaft is slidably disposed through the cap opening so as to form a plunger-head fluid-tight seal between the plunger shaft and a perimeter of the cap opening;

a solid-dosage-form support disc, which (a) is disposed below the bottom plunger wall so as to define a grinding compartment between the lower surface of the bottom plunger wall and an upper surface of the solid-dosage-form support disc, and (b) is shaped so as to define a plurality of holes through the solid-dosage-form support disc; and a knob;

inserting the solid dosage form into the grinding compartment;

thereafter, inserting the plunger head into the barrel such that (a) a portion of the barrel defines a closed-system syringe chamber between the bottom barrel wall and the lower surface of the bottom plunger wall, (b) the plunger-head annular seal forms a plunger-head fluid-tight seal between an outer surface of the plunger head and the cylindrical inner surface of the barrel;

thereafter, attaching the barrel cap to the top barrel opening so as to form a barrel-cap fluid-tight seal with the top barrel opening;

thereafter, while the closed-system grinding syringe is oriented upright, activating the knob such that the grinding compartment grinds the solid dosage form to a powder and at least 75% of the powder passes through the plurality of holes into a portion of the closed-system syringe chamber below the solid-dosage-form support disc;

thereafter, introducing a liquid into the closed-system syringe chamber via the fluid port;

thereafter, mixing the powder with the liquid to form a mixture; and thereafter, delivering the mixture via the fluid port by moving the plunger head downward within the barrel.

For some applications, introducing the liquid into the closed-system syringe chamber via the fluid port including coupling a syringe to the fluid port and injecting the liquid from the syringe into the closed-system syringe chamber via the fluid port.

For some applications, the closed-system grinding syringe is configured to move the lower surface of the bottom plunger wall and the upper surface of the solid-dosage-form support disc closer to each other as the grinding compartment grinds the solid dosage form.

For some applications, the closed-system grinding syringe is configured such that the lower surface of the bottom plunger wall does not rotate while the lower surface of the bottom plunger wall and the upper surface of the solid-dosage-form support disc move closer to each other as the grinding compartment grinds the solid dosage form.

For some applications, the closed-system grinding syringe is configured to move the upper surface of the solid-dosage-form support disc with respect to the cylindrical inner surface of the barrel as the grinding compartment grinds the solid dosage form.

For some applications, the closed-system grinding syringe is configured such that the upper surface of the solid-dosage-form support disc does not rotate during upward movement of the dosage-form support disc with respect to the cylindrical inner surface of the barrel.

For some applications, activating the knob includes rotating the knob.

For some applications, the closed-system grinding syringe is shaped so as to define a liquid channel having (a) a first liquid-channel opening in fluid communication with the fluid port and (b) a second liquid-channel opening in fluid communication with the closed-system syringe chamber.

For some applications:

the closed-system grinding syringe is shaped so as to define (a) a liquid channel having (i) a first liquid-channel opening in fluid communication with the fluid port and (ii) a second liquid-channel opening in fluid communication with the closed-system syringe chamber, and (b) a gas channel having a first gas-channel opening in fluid communication with the fluid port, and introducing the liquid into the closed-system syringe chamber via the fluid port includes coupling two needles of a dual-needle closed-pressure equalization syringe in fluid communication with the liquid channel and the gas channel, respectively, via the fluid port.

For some applications:

the barrel is shaped so as to define an upper compartment between the barrel cap and the bottom plunger wall, when the barrel cap is attached to the top barrel opening, wherein the upper compartment is fluid-isolated from the closed-system syringe chamber and the external environment, the liquid channel has a second liquid-channel opening in fluid communication with the closed-system syringe chamber through the bottom barrel wall, and the gas channel has a second gas-channel opening in fluid communication with the upper compartment.

For some applications, at least a portion of the upper compartment is located within the plunger head.

For some applications, the liquid channel has a greater average inner diameter than does the gas channel.

For some applications, the grinding compartment is shaped so as to define one or more lateral openings, and inserting the solid dosage form into the grinding compartment includes inserting the solid dosage form via the one or more lateral openings.

For some applications, delivering the mixture includes coupling the fluid port to a feeding tube and delivery the mixture to the feeding tube.

For some applications, the feeding tube is selected from the group consisting of: a universal feeding tube, a percutaneous endoscopic gastrostomy (PEG) tube, a gastrostomy tube, and a nasogastric feeding tube.

For some applications, delivering the mixture includes sealingly coupling an adapter to the fluid port and to the feeding tube.

For some applications, the feeding tube is selected from the group consisting of: a universal feeding tube, a percutaneous endoscopic gastrostomy (PEG) tube, a gastrostomy tube, and a nasogastric feeding tube.

There is still further provided, in accordance with an application of the present invention, apparatus including a closed-system grinding syringe for liquefying and delivering a solid dosage form, closed-system grinding syringe including:

a barrel, which is shaped so as to define (a) a lateral wall shaped so as to define a cylindrical inner surface, (b) a top barrel opening, and (c) a bottom barrel wall;

a fluid port disposed on the bottom barrel wall;

a plunger, which includes (a) a plunger shaft; (b) a plunger head shaped so as to define a bottom plunger wall shaped so as to define a lower surface; and (c) a plunger-head annular seal, wherein the plunger head is insertable into and moveable within the barrel such that (a) a portion of the barrel defines a closed-system syringe chamber between the bottom barrel wall and the lower surface of the bottom plunger wall, and (b) the plunger-head annular seal forms a plunger-head fluid-tight seal between an outer surface of the plunger head and the cylindrical inner surface of the barrel;

a grinding compartment; and a knob, wherein the closed-system grinding syringe is configured such that when (a) the solid dosage form is disposed in the grinding compartment, (b) the plunger head is inserted into the barrel, and (c) the closed-system grinding syringe is oriented upright, upon activation of the knob, the grinding compartment grinds the solid dosage form to a powder, and wherein the closed-system grinding syringe is shaped so as to define:

a liquid channel having (a) a first liquid-channel opening in fluid communication with the fluid port, and a gas channel having (a) a first gas-channel opening in fluid communication with the fluid port.

For some applications, the liquid channel has a greater average inner diameter than does the gas channel.

For some applications, the closed-system grinding syringe further includes a barrel cap, which is configured to be attachable to the top barrel opening so as to form a barrel-cap fluid-tight seal with the top barrel opening.

For some applications:

the barrel is shaped so as to define an upper compartment between the barrel cap and the bottom plunger wall, when the barrel cap is attached to the top barrel opening, wherein the upper compartment is fluid-isolated from the closed-system syringe chamber and the external environment, the liquid channel has a second liquid-channel opening in fluid communication with the closed-system syringe chamber through the bottom barrel wall, and the gas channel has a second gas-channel opening in fluid communication with the upper compartment.

For some applications, at least a portion of the upper compartment is located within the plunger head.

For some applications, the barrel cap is shaped so as to define a cap opening through the barrel cap, and the plunger shaft is slidably disposed through the cap opening so as to form a plunger-head fluid-tight seal between the plunger shaft and a perimeter of the cap opening.

For some applications, the closed-system grinding syringe further includes a solid-dosage-form support disc, which (a) is disposed below the bottom plunger wall such that the closed-system syringe chamber defines the grinding compartment between the lower surface of the bottom plunger wall and an upper surface of the solid-dosage-form support disc, and (b) is shaped so as to define a plurality of holes through the solid-dosage-form support disc.

For some applications, the closed-system grinding syringe is configured such that when (a) the solid dosage form is disposed in the grinding compartment, (b) the plunger head is inserted into the barrel, and (c) the closed-system grinding syringe is oriented upright, upon activation of the knob, the grinding compartment grinds the solid dosage form to the powder and at least 75% of the powder passes through the plurality of holes into a portion of the closed-system syringe chamber below the solid-dosage-form support disc.

The present invention will be more fully understood from the following detailed description of embodiments thereof, taken together with the drawings, in which:

BRIEF DESCRIPTION OF THE DRAWINGS

FIGS. 4A-L are schematic illustrations of a method of using the closed-system grinding syringe of FIG. 1 for liquefying and delivering a solid dosage form, in accordance with an application of the present invention;

DETAILED DESCRIPTION OF APPLICATIONS

Figure 1:
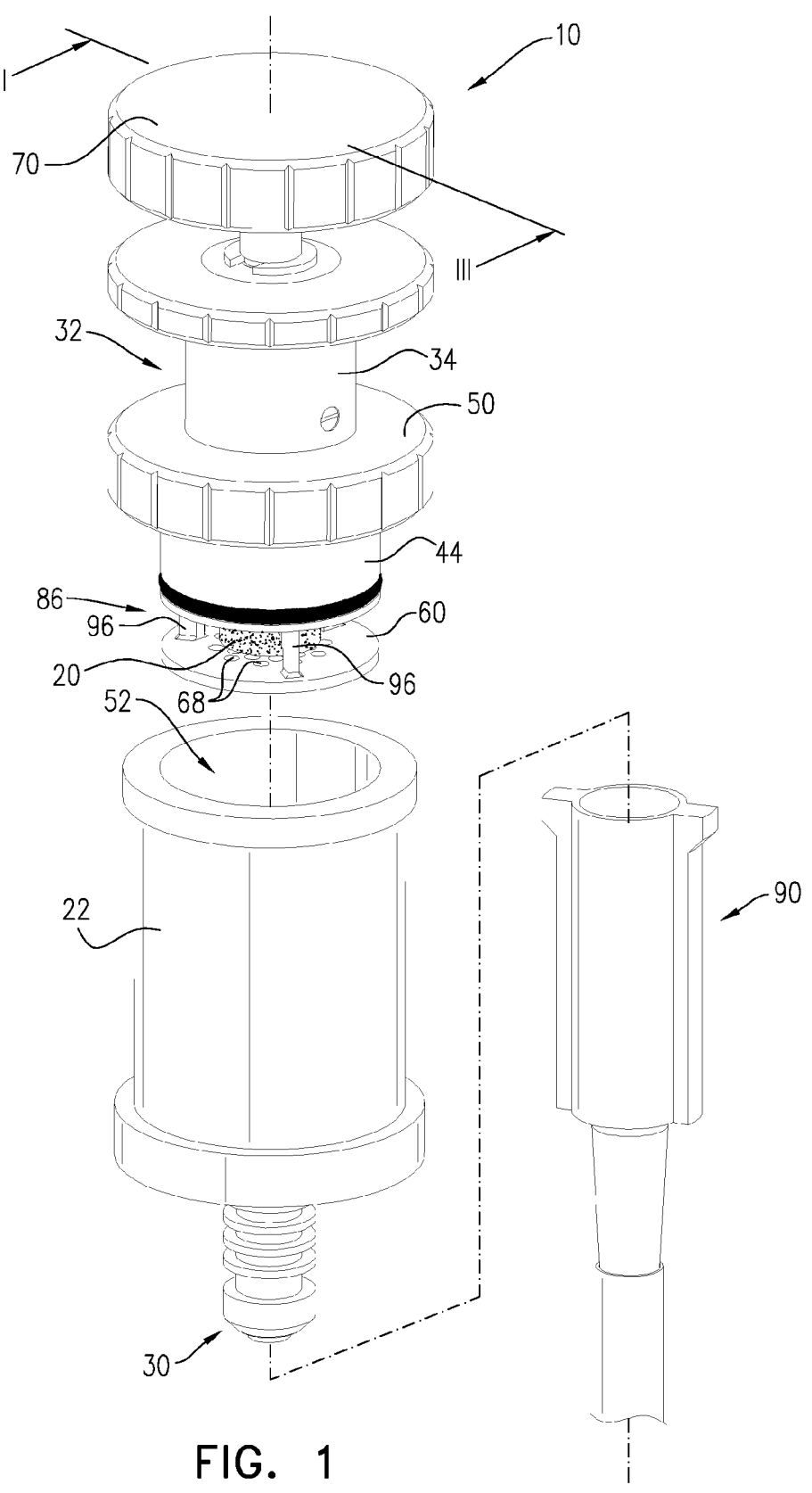
FIG. 1 is a schematic cross-sectional illustration of a closed-system grinding syringe for liquefying and delivering a solid dosage form, in accordance with an application of the present invention.

Reference is made to FIG. 1, which is a schematic cross-sectional illustration of a closed-system grinding syringe 10 for liquefying and delivering a solid dosage form 20, in accordance with an application of the present invention. FIG. 1 also shows an adapter 90, described hereinbelow. As used in the present application, including in the claims, "grinding" means reducing to a powder comprising small (e.g., fine) particles, as by pounding, crushing, or pulverizing. Typically, the particle size is less than 2 mm.

Figures 2A, 2B:
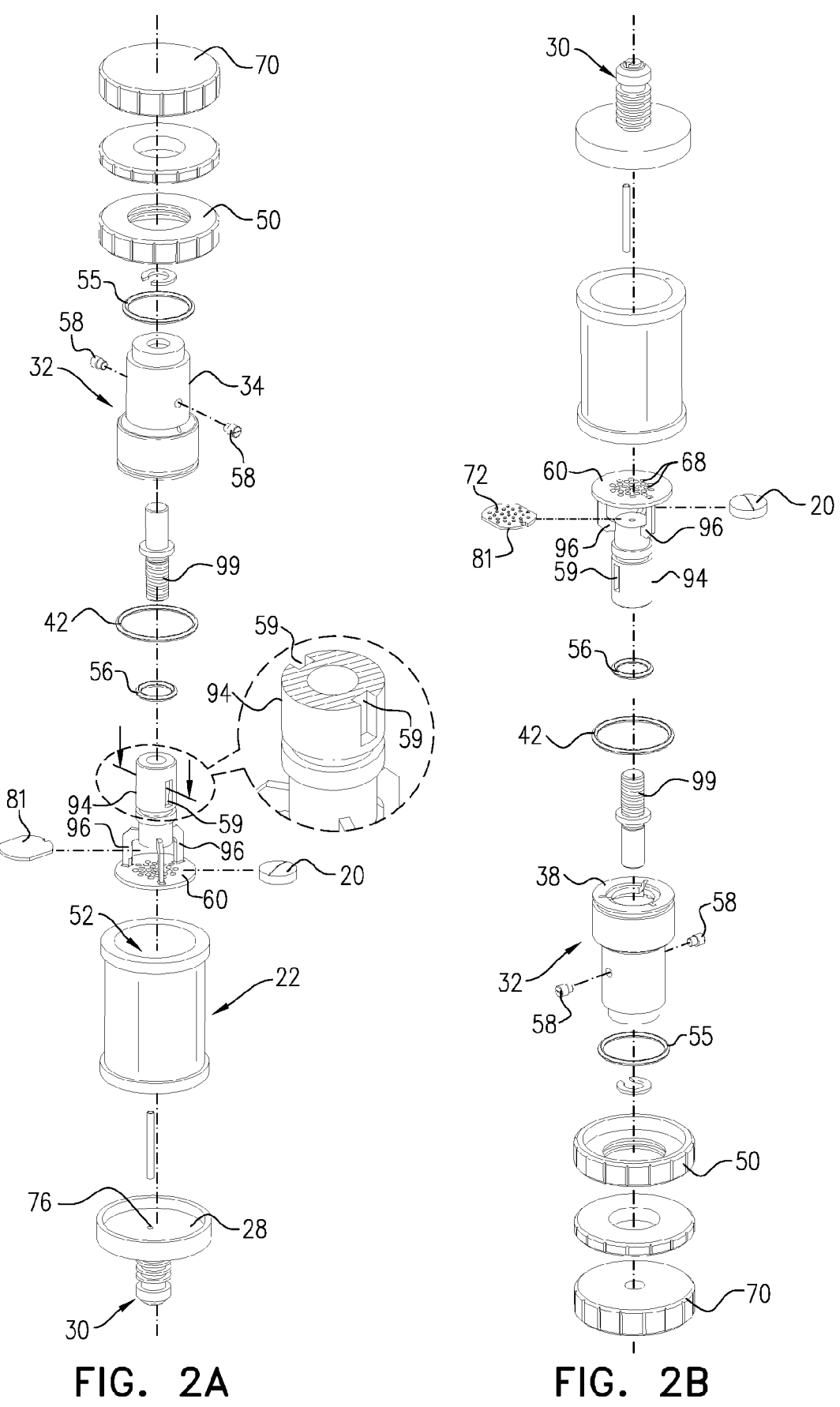
FIGS. 2A-B are exploded schematic illustrations showing components of the closed-system grinding syringe of FIG. 1, in accordance with an application of the present invention.

Reference is also made to FIGS. 2A-B, which are exploded schematic illustrations showing components of closed-system grinding syringe 10, in accordance with an application of the present invention. The components closed-system grinding syringe 10 may comprise a metal, such as stainless steel, and/or a polymer.

Figure 3:
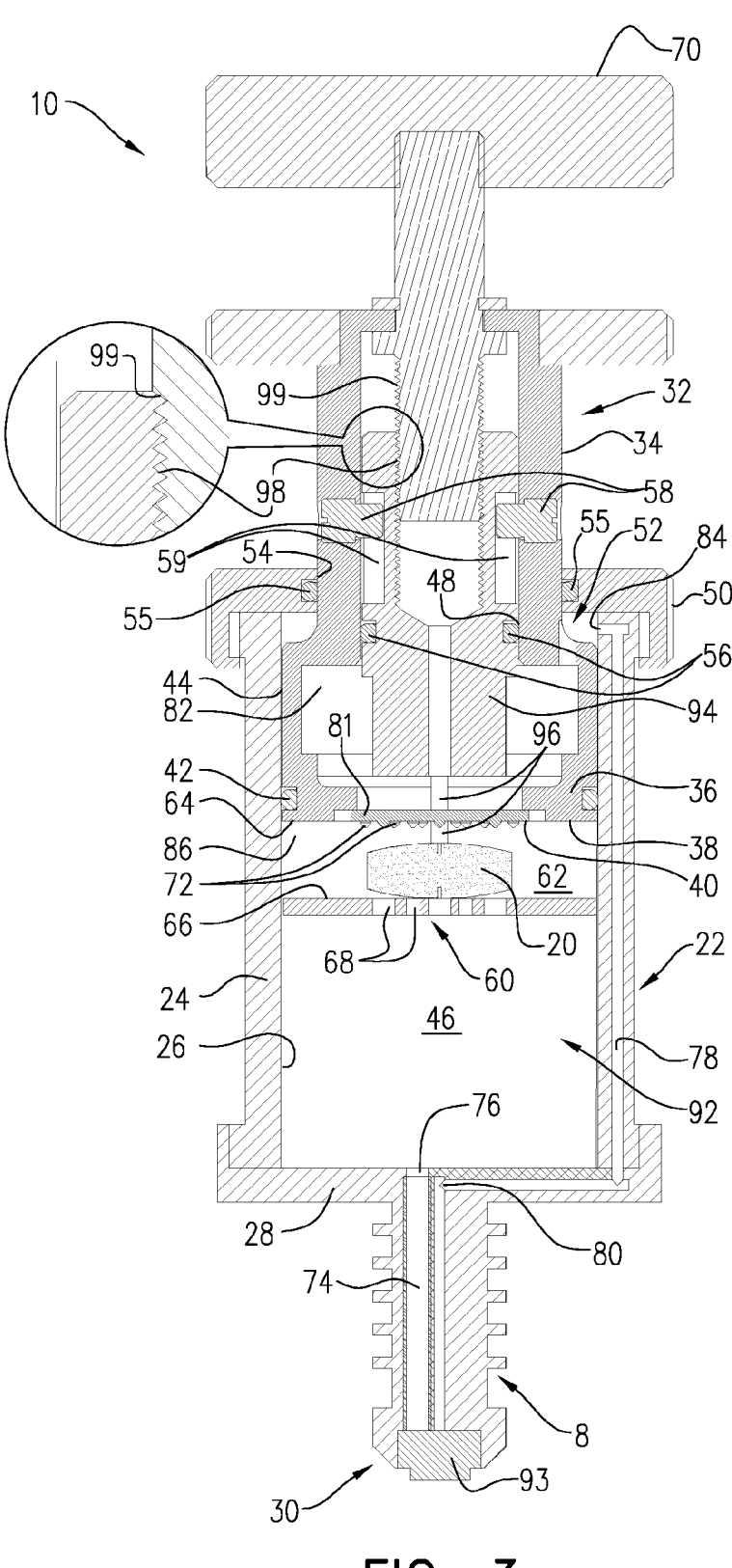
FIG. 3 is a schematic cross-sectional view of the closed-system grinding syringe of FIG. 1, in accordance with an application of the present invention.

Reference is further made to FIG. 3, which is a schematic cross-sectional view of closed-system grinding syringe 10, in accordance with an application of the present invention. Although not a component of closed-system grinding syringe 10, solid dosage form 20 is shown in FIGS. 1, 2A-B, and 3 for illustrating the operation of closed-system grinding syringe 10. In particular, solid dosage form 20 is shown in FIGS. 2A-B to illustrate the eventual location of solid dosage form 20; solid dosage form 20 is of course not inserted into closed-system grinding syringe 10 during manufacture of closed-system grinding syringe 10, but during use of the syringe by a healthcare worker after manufacture.

Typically, closed-system grinding syringe 10 comprises:

a barrel 22, which is shaped so as to define (a) a lateral wall 24 shaped so as to define a cylindrical inner surface 26, (b) a top barrel opening 52, and (c) a bottom barrel wall 28;

a fluid port 30 disposed on bottom barrel wall 28; and a plunger 32, which comprises (a) a plunger shaft 34; (b) a plunger head 36 shaped so as to define a bottom plunger wall 38 shaped so as to define a lower surface 40; and (c) a plunger-head annular seal 42 (comprising, for example, an O-ring or another resiliently elastic seal).

Plunger head 36 is insertable into and moveable within barrel 22 such that (a) a portion of barrel 22 defines a closed-system syringe chamber 46 between bottom barrel wall 28 and lower surface 40 of bottom plunger wall 38, and (b) that plunger-head annular seal 42 forms a plunger-head fluid-tight seal between an outer surface 44 of plunger head 36 and cylindrical inner surface 26 of barrel 22. Typically, plunger shaft 34 and plunger head 36 are arranged such that downward motion of plunger shaft 34 moves plunger head 36 downward within barrel 22.

For some applications, plunger 32 is non-integral with barrel 22, and separable from and coupleable to barrel 22 during normal use of closed-system grinding syringe 10. FIG. 1 (as well as FIGS. 4A-B) shows plunger 32 separated from barrel 22, while FIG. 3 (as well as FIGS. 4C-L) shows plunger 32 coupled to barrel 22 with plunger head 36 inserted into barrel 22. Alternatively, plunger 32 is integrated with barrel 22, in which case closed-system grinding syringe 10 is typically provided with plunger 32 maximally withdrawn from barrel, such that access is provided to grinding compartment 62, described hereinbelow.

Typically, plunger shaft 34 has a smaller average outer diameter than does plunger head 36.

Typically, closed-system grinding syringe 10 further comprises a barrel cap 50, which is configured to be attachable to top barrel opening 52 (such as by relative rotation) so as to form a barrel-cap fluid-tight seal with top barrel opening 52. Barrel cap 50 is shaped so as to define a cap opening 54 through barrel cap 50. Plunger shaft 34 is slidably disposed through cap opening 54 so as to form a plunger-head fluid-tight seal between plunger shaft 34 and a perimeter of cap opening 54 (such as by an annular seal 55, e.g., an O-ring). Typically, barrel cap 50 is fixed to plunger 32 such that plunger shaft 34 is slidably disposed through cap opening 54 and plunger 32 is not separable from barrel cap 50 during the normal use of closed-system grinding syringe 10.

Typically, closed-system grinding syringe 10 further comprises a solid-dosage-form support disc 60, which is disposed below bottom plunger wall 38 so as to define a grinding compartment 62 between a lower surface 64 of bottom plunger wall 38 and an upper surface 66 of solid-dosage-form support disc 60. (Solid-dosage-form support disc 60 is thus disposed within closed-system syringe chamber 46.) Solid-dosage-form support disc 60 is shaped so as to define a plurality of holes 68 through solid-dosage-form support disc 60. (Because of these holes 68, solid-dosage-form support disc 60 does not meaningfully disturb the fluid continuity of closed-system syringe chamber 46.) Typically, holes 68 have an average diameter of at least 1 mm (e.g., at least 2 mm), no more than 5 mm, and/or between 1 mm (e.g., 2 mm) and 5 mm, and/or an average cross-sectional area of at least 0.8 cm2 (e.g., at least 3.1 mm2), no more than 20 mm2, and/or between 0.8 mm2 (e.g., 3.1 mm2) and 20 mm2.

Typically, grinding compartment 62 is shaped so as to define one or more lateral openings 86 for insertion of solid dosage form 20 into grinding compartment 62 (insertion of plunger head 36 into barrel 22 typically causes cylindrical inner surface 26 of barrel 22 to partially or entirely obstruct the one or more lateral openings 86). For some applications, as shown, the one or more lateral openings 86 are a single lateral opening that extends 360 degrees around grinding compartment 62. Alternatively, for some applications, the one or more lateral openings 86 extend between 90 and 360 degrees around grinding compartment 62. Alternatively, grinding compartment 62 instead defines another type of opening, such as a door, window, or flap.

Typically, closed-system grinding syringe 10 further comprises a knob 70. Typically, knob 70 is coupled to a top end of plunger shaft 34. For some applications, closed-system grinding syringe 10 is configured such that knob 70 is activated by rotation thereof. As mentioned above, plunger shaft 34 and plunger head 36 are typically arranged such that downward motion of plunger shaft 34 moves plunger head 36 downward within barrel 22; typically, knob 70 and plunger shaft 34 are arranged such that downward motion of knob 70 moves down plunger shaft 34, and thus plunger head 36. Alternatively, for some applications, closed-system grinding syringe 10 is configured such that knob 70 is activated by axial movement of knob 70 (downward or upward) (configuration not shown).

For some applications, closed-system grinding syringe 10 is configured such that when (a) solid dosage form 20 is disposed in grinding compartment 62, (b) plunger head 36 is inserted into barrel 22, and (c) closed-system grinding syringe 10 is oriented upright (i.e., barrel cap 50 is disposed above bottom barrel wall 28), upon activation of knob 70, grinding compartment 62 grinds solid dosage form 20 to a powder 71 and at least 75% (e.g., at least 95%) of powder 71 passes through the plurality of holes 68 into a portion 92 of closed-system syringe chamber 46 below solid-dosage-form support disc 60.

For some applications, lower surface 40 of bottom plunger wall 38 is shaped so as to define grinding protrusions 72. For example, grinding protrusions 72 may comprise teeth, burrs, or an abraded surface. A protrusion support 81 may be provided that is shaped so as to define grinding protrusions 72, and to couple grinding protrusions 72 to plunger head 36, such that protrusion support 81 defines at least a portion of lower surface 40 of bottom plunger wall 38. For some applications, lower surface 40 is shaped so as to define between 10 and 100 grinding protrusions 72. Alternatively or additionally, for some applications, upper surface 66 of solid-dosage-form support disc 60 is shaped so as to define support-disc grinding protrusions, such as describe hereinbelow with reference to FIGS. 7A-C and 8A-B.

Typically, closed-system grinding syringe 10 is non-electrical and is configured such that when (a) solid dosage form 20 is disposed in grinding compartment 62, (b) plunger head 36 is inserted into barrel 22, and (c) closed-system grinding syringe 10 is oriented upright, upon mechanical activation of knob 70, grinding compartment 62 grinds solid dosage form 20.

For some applications, fluid port 30 comprises a valve 93. For example, the valve may comprise one or more self-sealing membranes, e.g., comprising silicone, rubber, or any other suitable materials for scaling.

For some applications, closed-system grinding syringe 10 is configured to move lower surface 40 of bottom plunger wall 38 and upper surface 66 of solid-dosage-form support disc 60 closer to each other as grinding compartment 62 grinds solid dosage form 20. For example, closed-system grinding syringe 10 may be configured to move upper surface 66 of solid-dosage form with respect to cylindrical inner surface 26 of barrel 22 as grinding compartment 62 grinds solid dosage form 20.

For some applications, closed-system grinding syringe 10 further comprises:
an axially-moveable shaft 94, which (a) is disposed partially within plunger shaft 34, (b) forms a fluid-tight seal with an inner surface 48 of plunger shaft 34 (such as by an annular seal 56, e.g., an O-ring), (c) is connected to solid-dosage-form support disc 60, such as by one or more connection arms 96, e.g., three connection arms 96, (d) is rotationally-fixed with respect to plunger shaft 34, and (e) is shaped so as to define an inner space having an internally-threaded wall 98; and an externally-threaded stem 99, which is (a) disposed partially within plunger shaft 34, (b) axially fixed with respect to plunger shaft 34, and (c) connected to knob 70. The external thread of externally-threaded stem 99 is mated with the internal thread of internally-threaded wall 98, such that rotation of externally-threaded stem 99 in one rotational direction (e.g., clockwise) (such as by rotation of knob 70) causes upward axial movement of axially-moveable shaft 94 with respect to plunger shaft 34, which in turn moves upper surface 66 of solid-dosage-form support disc 60 upward with respect to cylindrical inner surface 26 of barrel 22, causing grinding compartment 62 to grind solid dosage form 20 by squeezing and squashing solid dosage form 20 between upper surface 66 of solid-dosage-form support disc 60 and lower surface 40 of bottom plunger wall 38. It is noted that a relatively large amount of force is applied to solid dosage form 20 by this rotational arrangement. Typically, closed-system grinding syringe 10 is configured such that upper surface 66 of solid-dosage-form support disc 60 and lower surface 40 of bottom plunger wall 38 can come very close to each other, typically touch each other, if not blocked by remnants of solid dosage form 20 that fail to pass through holes 68.

Typically, upper surface 66 of solid-dosage-form support disc 60 does not rotate during upward movement of solid-dosage-form support disc 60 with respect to cylindrical inner surface 26 of barrel 22, i.e., is rotationally fixed with respect to lower surface 40 of bottom plunger wall 38 and with respect to cylindrical inner surface 26 of barrel 22 (as well as with respect to other components of closed-system grinding syringe 10). In addition, lower surface 40 of bottom plunger wall 38 typically does not rotate while lower surface 40 of bottom plunger wall 38 and upper surface 66 of solid-dosage-form support disc 60 move closer to each other as grinding compartment 62 grinds solid dosage form 20 by squeezing and squashing solid dosage form 20 between upper surface 66 of solid-dosage-form support disc 60 and lower surface 40 of bottom plunger wall 38; i.e., lower surface 40 of bottom plunger wall 38 is rotationally fixed with respect to upper surface 66 of solid-dosage-form support disc 60 (as well as with respect to other components of closed-system grinding syringe 10).

For example, axially-moveable shaft 94 may be rotationally-fixed with respect to plunger shaft 34 by one or more set screws 58 that engage one or more corresponding axial depressions 59 defined by an outer surface of axially-moveable shaft 94. Alternative ways of rotationally fixing axially-moveable shaft 94 with respect to plunger shaft 34 will readily be apparent to those skilled in the art who have read the present application.

Reference is now made to FIGS. 4A-L, which are schematic illustrations of a method of using closed-system grinding syringe 10 for liquefying and delivering solid dosage form 20, in accordance with an application of the present invention.

The method begins with the receipt of closed-system grinding syringe 10 by the healthcare worker, optionally with plunger head 36 pre-inserted into barrel 22. Alternatively, the syringe is packaged with plunger head 36 separate from barrel 22. If plunger head 36 is received pre-inserted into barrel 22, the healthcare worker removes plunger head 36 from barrel 22.

Figure 4B:
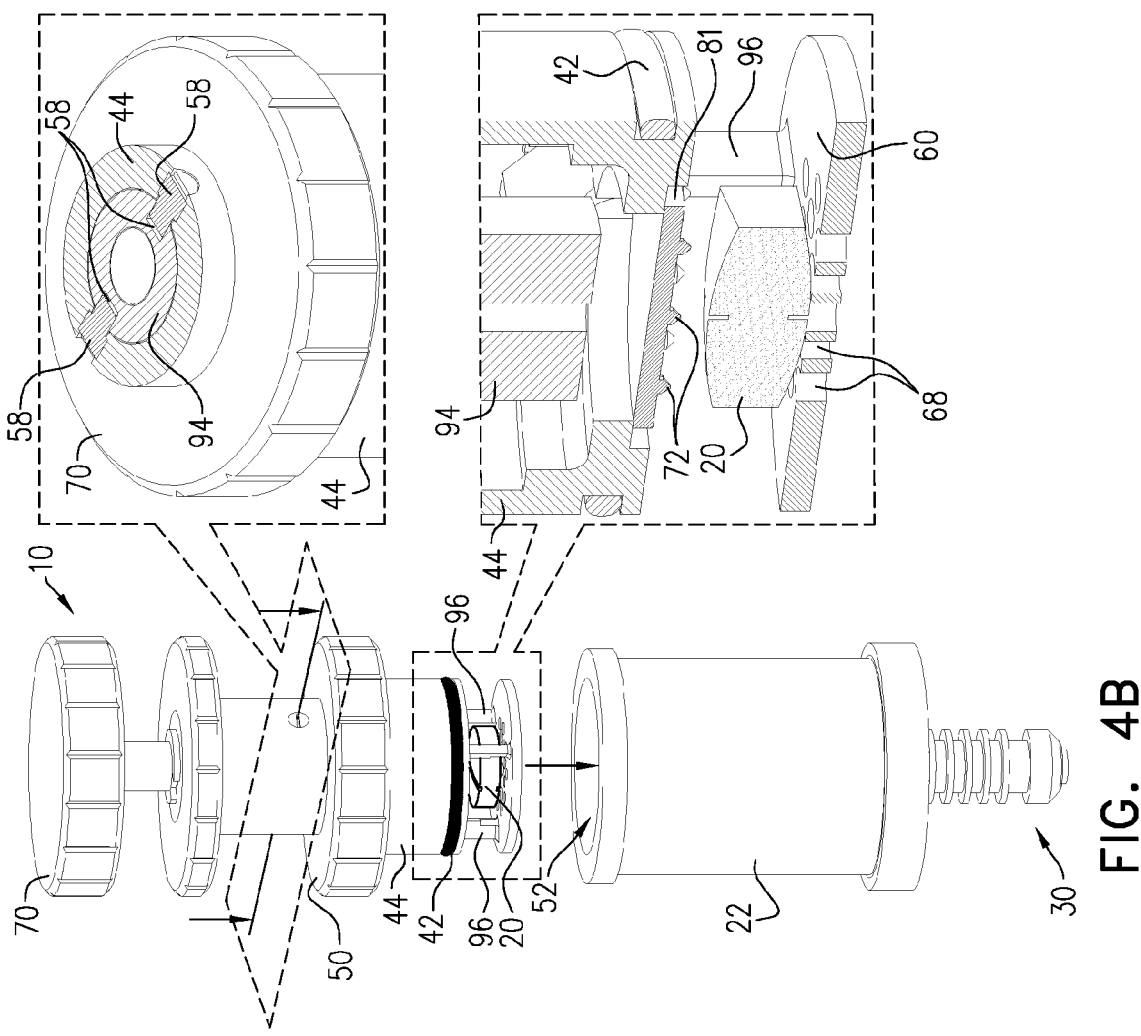
Figure 4A:
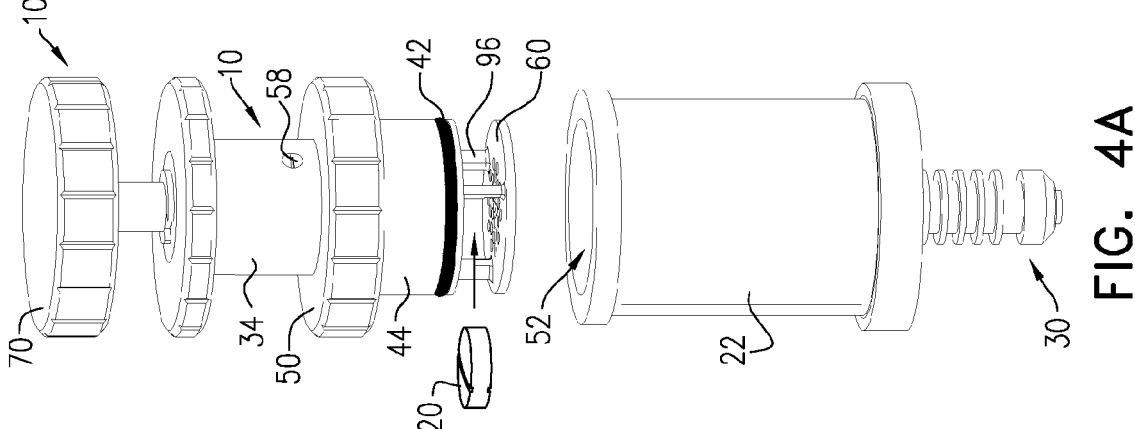

As shown in FIGS. 4A-B, the healthcare worker inserts solid dosage form 20 into grinding compartment 62. For example, solid dosage form 20 may comprise one or more drug pills, drug capsule, or any other solid dosage form.

Figure 4C:
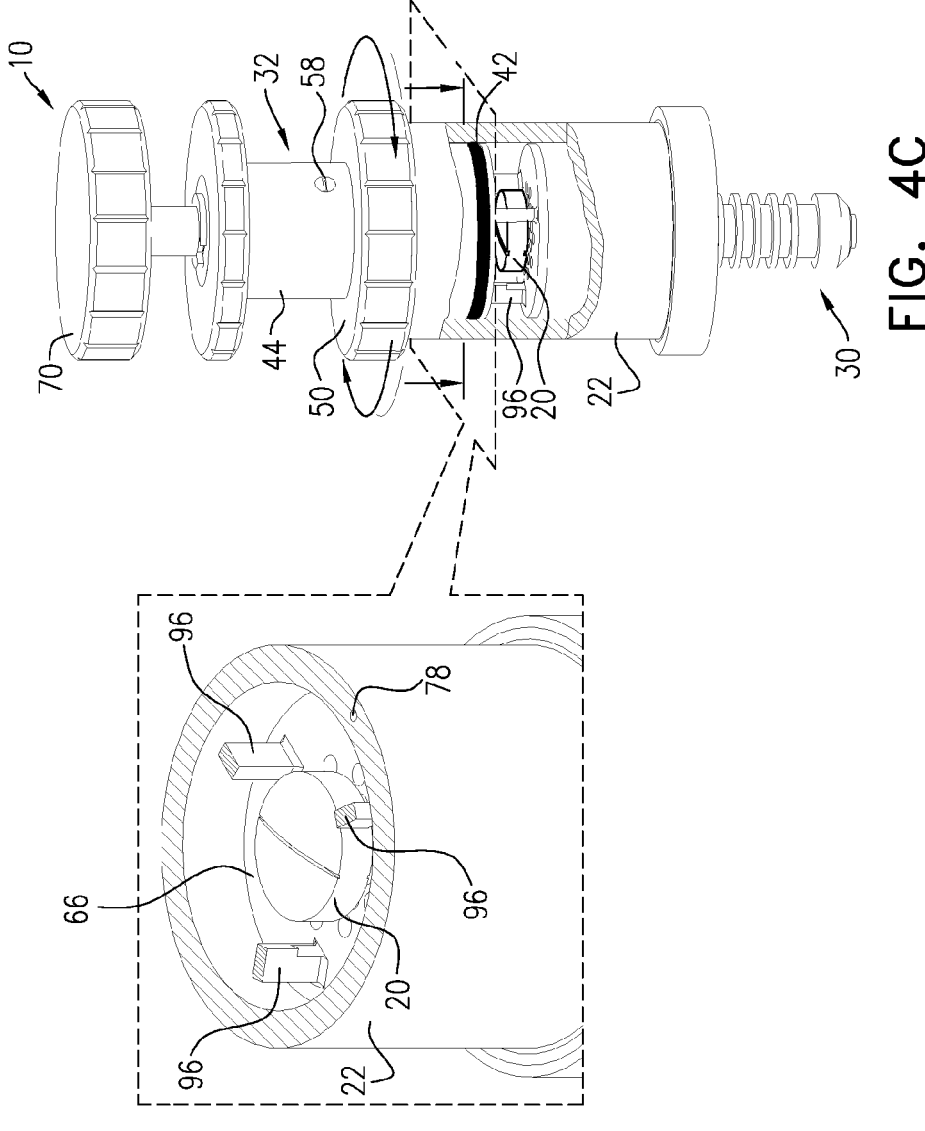
Figures 4D, 4E:
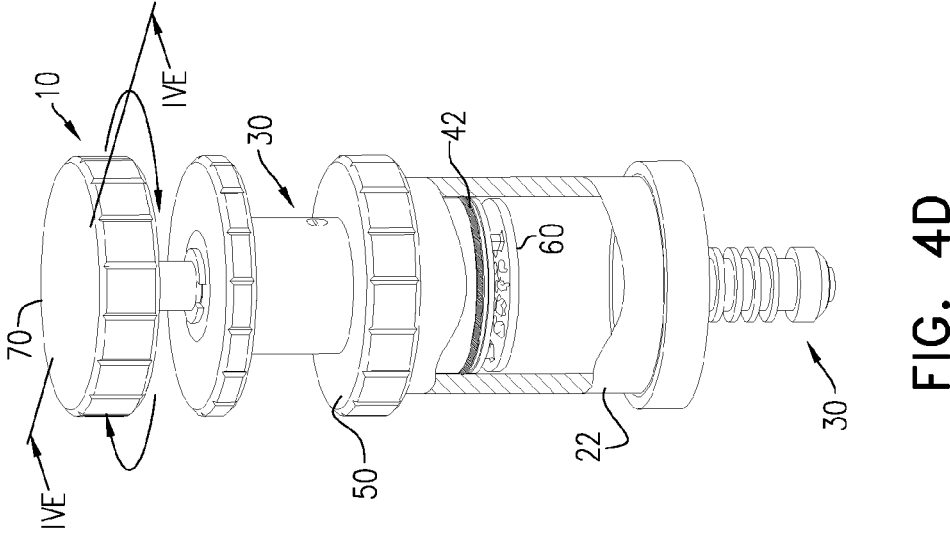

Thereafter, as shown in FIG. 4C, the healthcare worker inserts (a) plunger head 36 into barrel 22 such that a portion of barrel 22 defines closed-system syringe chamber 46 between bottom barrel wall 28 and lower surface 40 of bottom plunger wall 38, and (b) attaches barrel cap 50 to top barrel opening 52 so as to form a barrel-cap fluid-tight seal with top barrel opening 52. Solid dosage form 20 is not yet ground into powder 71 at this step of the method.

Thereafter, as shown in FIGS. 4D-G, while closed-system grinding syringe 10 is oriented upright, the healthcare worker activates knob 70 (such as by rotation) such that grinding compartment 62 grinds solid dosage form 20 to powder 71 and at least 75% (e.g., at least 95%) of powder 71 passes through the plurality of holes 68 into portion 92 of closed-system syringe chamber 46 below solid-dosage-form support disc 60.

Figure 4G:
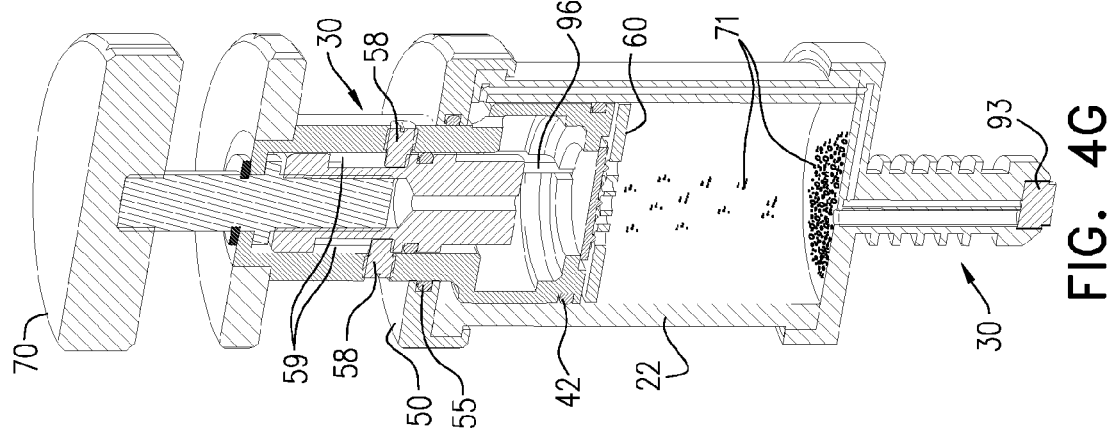
Figure 4F:
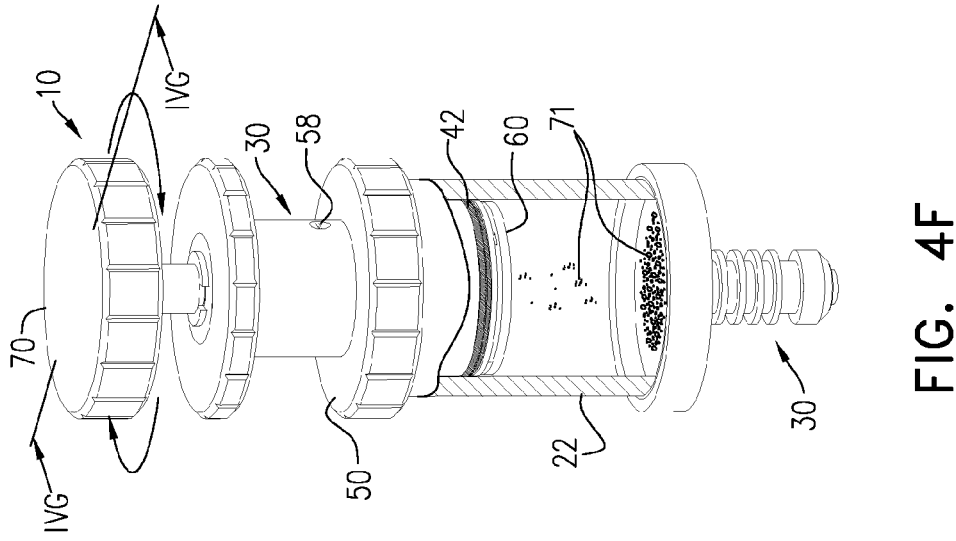
Figures 4H, 4I:
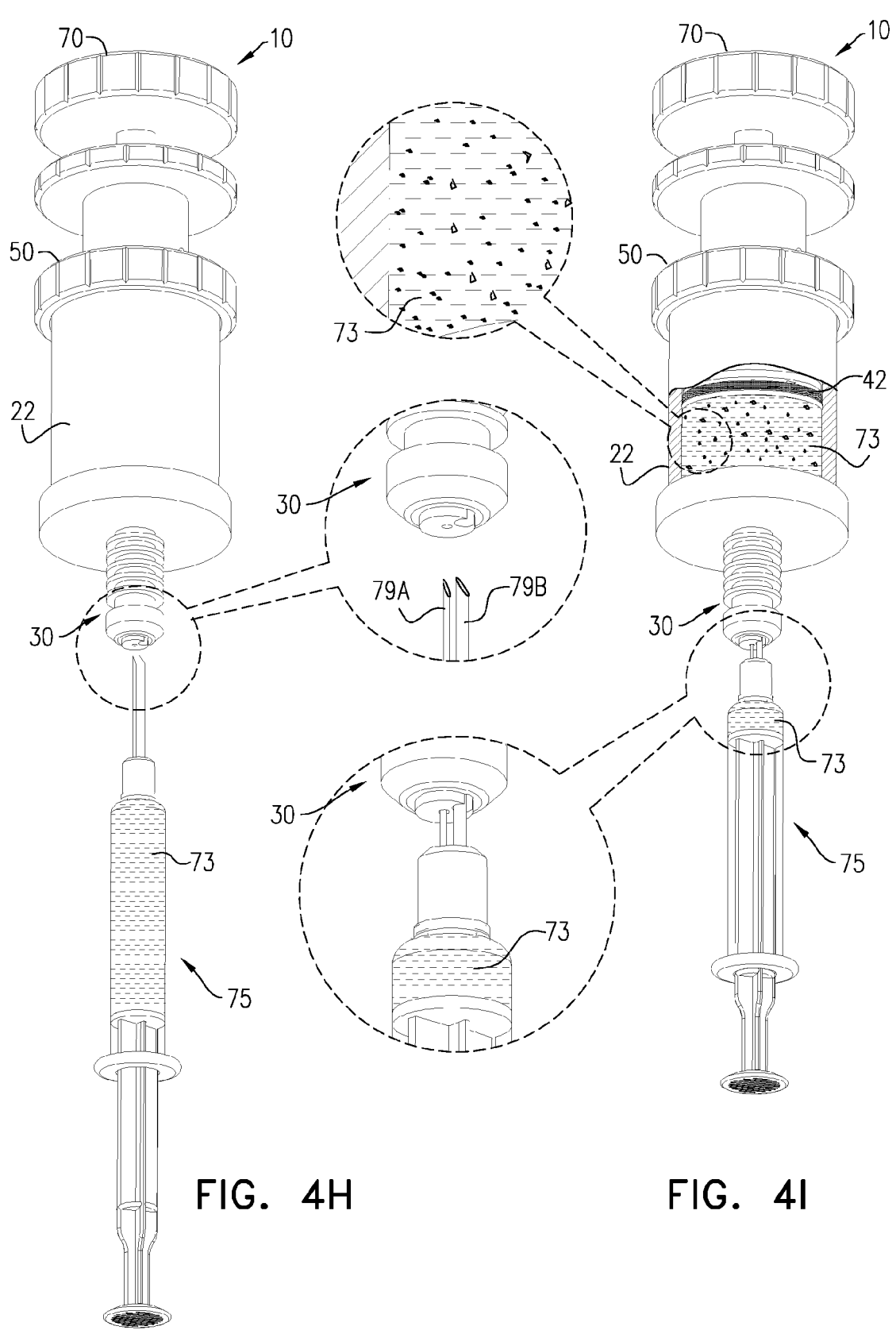

Thereafter, as shown in FIGS. 4H-I, the healthcare worker introduces (e.g., injects) a liquid 73 into closed-system syringe chamber 46 via fluid port 30.

For some applications, fluid port 30 is configured to mate with a tip of a syringe 75 (separate from closed-system grinding syringe 10), for introducing liquid 73 into closed-system syringe chamber 46 via fluid port 30. For example, fluid port 30 may be shaped so as to define a female-taper fitting, such as a Luer lock or a Luer taper, as are known in the art.

Figure 4J:
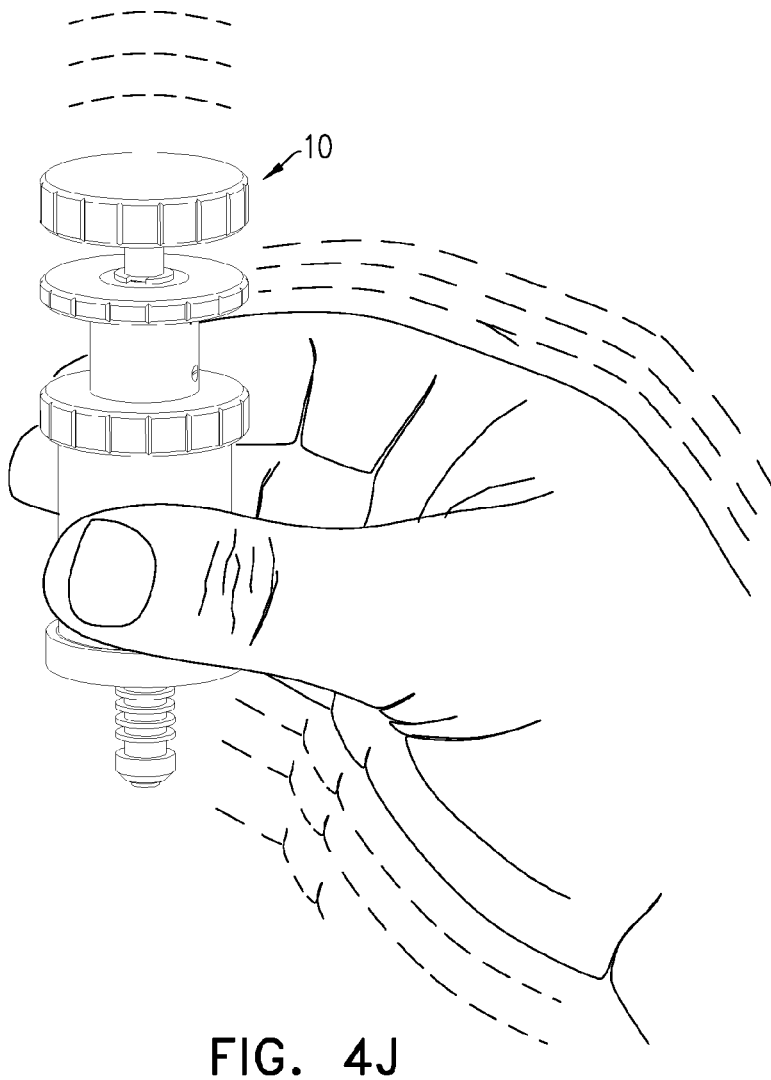

Thereafter, as shown in FIG. 4J, powder 71 is mixed with liquid 73 to form a mixture 77 (e.g., a solution or a suspension), such as by shaking closed-system grinding syringe 10. It is noted that before mixing generally most of powder 71 is loose at the bottom of closed-system syringe chamber 46, which facilitates mixing more readily than if, for example, powder 71 were crushed into a cake during the grinding process. Typically, during this mixing, all or a portion of powder 71 that may have remained above solid-dosage-form support disc 60 during grinding, as described hereinabove with reference to FIG. 4G, is washed through holes 68 into portion 92 of closed-system syringe chamber 46 below solid-dosage-form support disc 60. Optionally, after mixing, the healthcare worker again activates knob 70 such that grinding compartment 62 grinds any small remaining pieces of solid dosage form 20 to powder 71, and then mixes again, such that essentially 100% of powder 71 (and thus solid dosage form 20) eventually passes through holes 68 into portion 92 of closed-system syringe chamber 46 below solid-dosage-form support disc 60.

Thereafter, as shown in FIGS. 4K-L, the healthcare worker delivers mixture 77 via fluid port 30 by moving plunger head 36 downward within barrel 22.

For some applications, bottom barrel wall 28 is shaped as a funnel (typically a shallow funnel), similar to the bottom surface of conventional syringe chambers, in order to allow more thorough delivery of mixture 77 from barrel 22 to fluid port 30. For some of these applications, the bottom surface of solid-dosage-form support disc 60 is slightly convex (e.g., inverse-funnel shaped), similar to the bottom surface of a conventional syringe plunger, in order to fit snugly into the funnel-shaped bottom barrel wall 28 and increase delivery of mixture 77 from barrel 22.

For some applications, fluid port 30 is configured to mate with a feeding tube, for delivering mixture 77 via fluid port 30. For example, the feeding tube may be a universal feeding tube, a percutaneous endoscopic gastrostomy (PEG) tube, a gastrostomy tube, or a nasogastric feeding tube. Alternatively, mixture 77 may be delivered the patient's mouth, without a feeding tube. In general, closed-system grinding syringe 10 may be useful for liquifying solid drug forms for patients who cannot swallow solid drugs.

For some applications, as shown in FIGS. 1 and 4K-L, a system is provided that comprises closed-system grinding syringe 10 and adapter 90, which is configured to be sealingly coupled to fluid port 30 and to a feeding tube. For example, the feeding tube may be a universal feeding tube, a percutaneous endoscopic gastrostomy (PEG) tube, a gastrostomy tube, or a nasogastric feeding tube. Alternatively, mixture 77 may be delivered the patient's mouth, without a feeding tube.

Reference is again made to FIG. 3. For some applications, closed-system grinding syringe 10 is shaped so as to define:

a liquid channel 74 having (a) a first liquid-channel opening 76 in fluid communication with fluid port 30 and (b) a second liquid-channel opening 76 in fluid communication with closed-system syringe chamber 46, and a gas channel 78 having (a) a first gas-channel opening 80 in fluid communication with fluid port 30.

Optionally, liquid channel 74 has a greater average inner diameter than does gas channel 78.

For some applications, barrel 22 is shaped so as to define an upper compartment 82 between barrel cap 50 and bottom plunger wall 38, at least when barrel cap 50 is attached to top barrel opening 52. Upper compartment 82 is fluid-isolated from closed-system syringe chamber 46 and from the external environment. For some applications, at least a portion of (e.g., an entirety of) upper compartment 82 is located within plunger head 36.

For some applications, second liquid-channel opening 76 of liquid channel 74 is in fluid communication with closed-system syringe chamber 46 through bottom barrel wall 28, and gas channel 78 has a second gas-channel opening 84 in fluid communication with upper compartment 82.

Providing liquid channel 74 and gas channel 78 enables, for the introduction of liquid 73 into closed-system syringe chamber 46 via fluid port 30 described hereinabove with reference to FIGS. 4H-I, the mating of fluid port 30 with a tip of a dual-needle closed-pressure equalization syringe comprising needles 79A and 79B, such that two needles of the dual-needle closed-pressure equalization syringe are in fluid communication with liquid channel 74 and gas channel 78, respectively, via fluid port 30. For example, dual-needle closed-pressure equalization syringes are described in U.S. Pat. No. 9,999,569 to Kriheli, U.S. Pat. No. 8,196,614 to Kriheli, and US Patent Application Publication 2019/0060170 to Kriheli et al., all of which are incorporated hereby reference; and Equashield® for liquid oral dosage forms is commercially available from Equashield LLC, Port Washington, NY, USA). The use of a dual-needle closed-pressure equalization syringe allows the injection of liquid 73 from a liquid compartment of the dual-needle closed-pressure equalization syringe into liquid channel 74 and the simultaneous return of gas from gas channel 78 into a separate gas compartment in the dual-needle closed-pressure equalization syringe.

Figure 5:
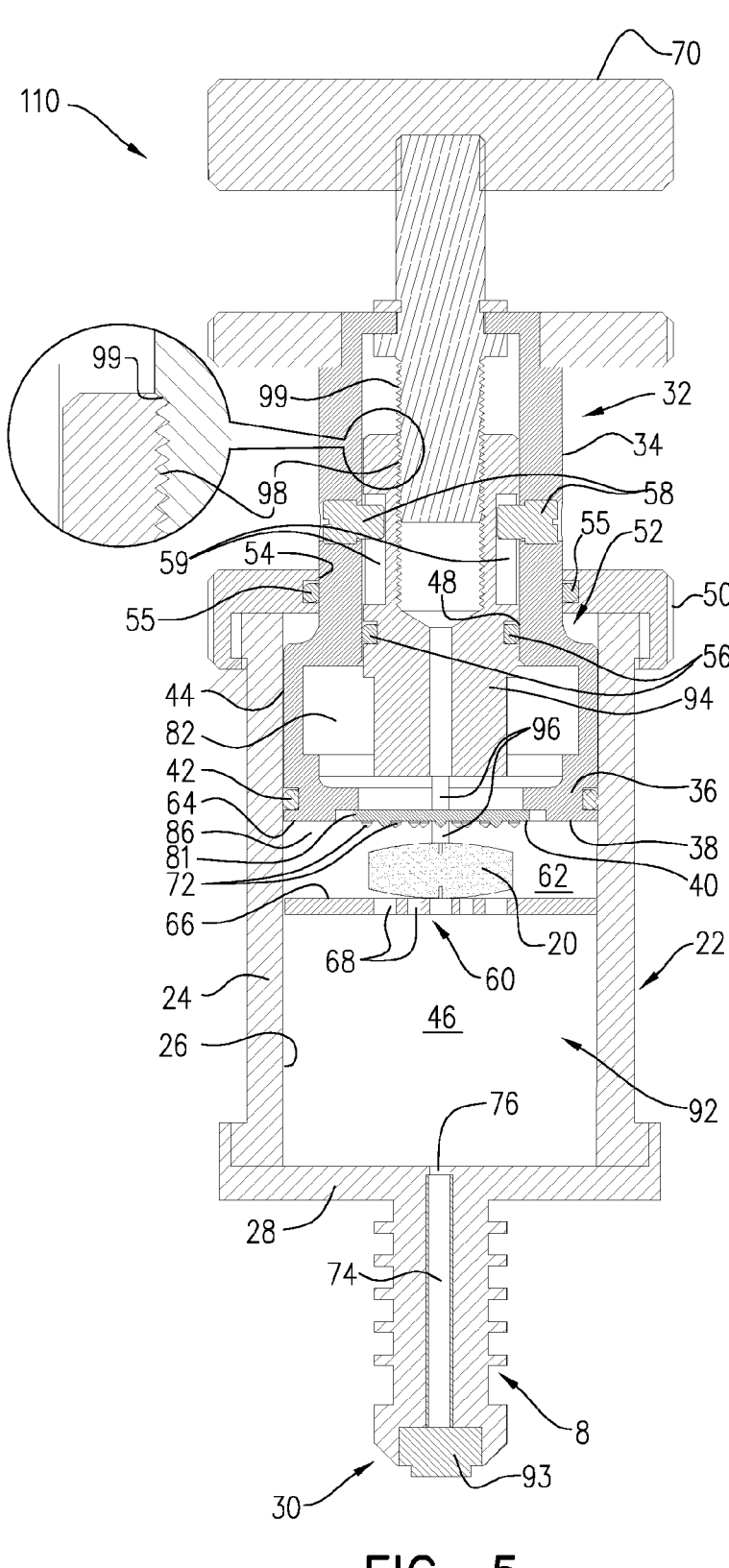
FIG. 5 is a schematic illustration of another closed-system grinding syringe for liquefying and delivering a solid dosage form, in accordance with an application of the present invention.
Figures 6A, 6B:
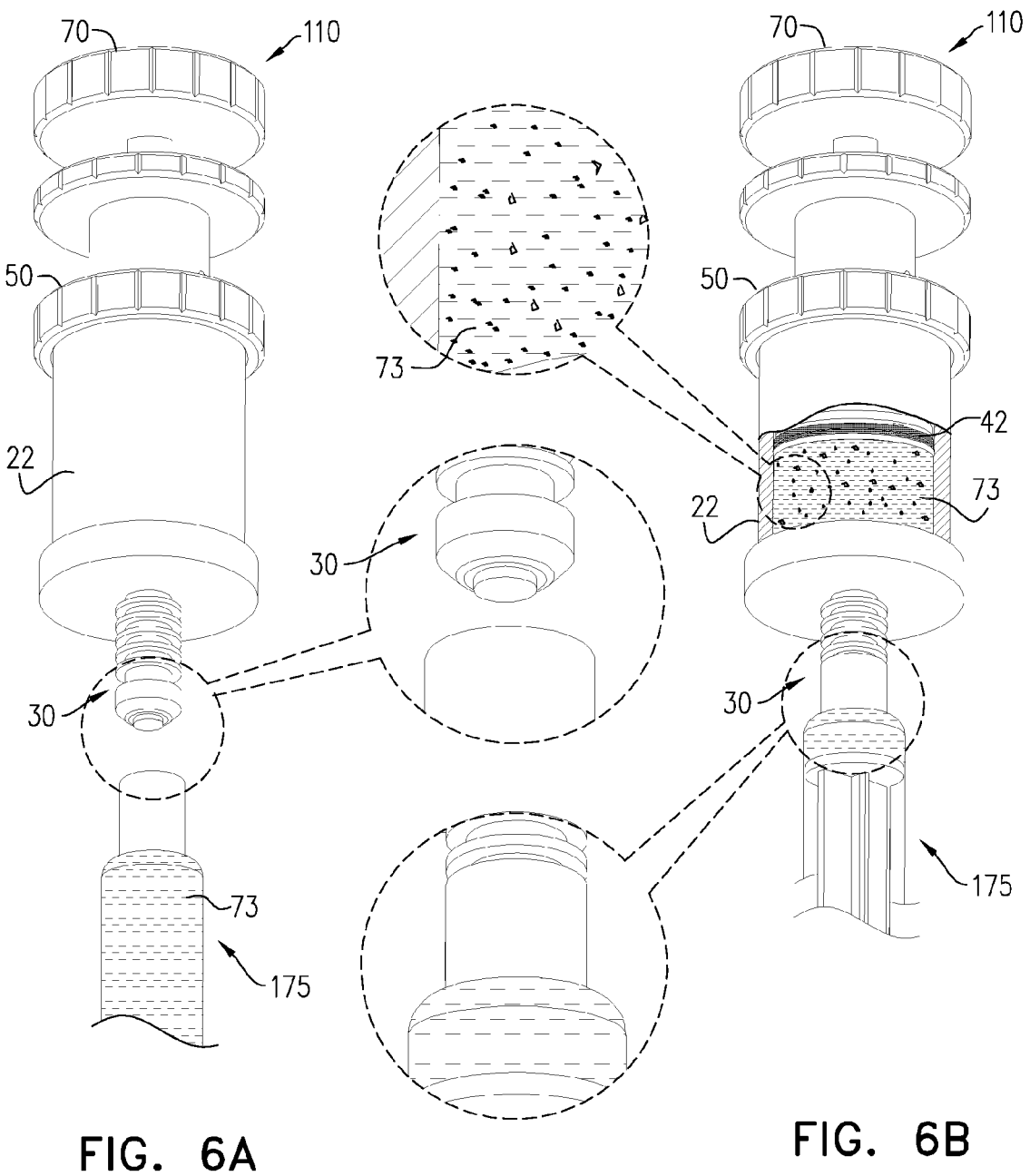
FIGS. 6A-B are schematic illustrations of a portion of a method of using the closed-system grinding syringe of FIG. 5 for liquefying and delivering the solid dosage form, in accordance with an application of the present invention.

Reference is now made to FIG. 5, which is a schematic illustration of a closed-system grinding syringe 110 for liquefying and delivering solid dosage form 20, in accordance with an application of the present invention. Reference is also made to FIGS. 6A-B, which are schematic illustrations of a portion of a method of using closed-system grinding syringe 110 for liquefying and delivering solid dosage form 20, in accordance with an application of the present invention. Other than as described hereinbelow, closed-system grinding syringe 110 may be identical to closed-system grinding syringe 10, described hereinabove with reference to FIGS. 1-4L, may be used in the same manner, and may implement any of the features thereof described herein.

Unlike closed-system grinding syringe 10, closed-system grinding syringe 10 is not shaped so as to define gas channel 78. Instead of introducing liquid 73 into closed-system syringe chamber 46 as described hereinabove with reference to FIGS. 4H-I, the healthcare worker introduces (e.g., injects) liquid 73 into closed-system syringe chamber 46 via fluid port 30 by mating a tip of a single-channel syringe 175 (which is separate from closed-system grinding syringe 10, and is typically conventional). For example, fluid port 30 may be shaped so as to define a female-taper fitting, such as a Luer lock or a Luer taper, and syringe 175 may be shaped so as to define a male-taper fitting, such as a Luer lock or a Luer taper, as are known in the art. It is noted that the air in closed-system syringe chamber 46 prior to introduction of liquid 73 is sufficiently compressible such that the force necessary to introduce liquid 73 can be readily applied manually by the healthcare worker.

Figure 7A:
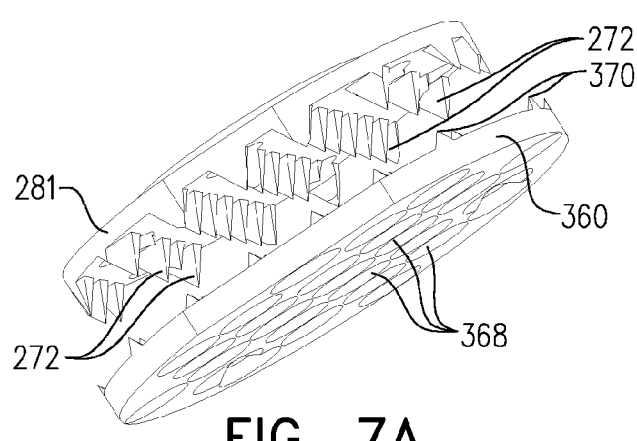
FIGS. 7A-C are schematic illustrations of alternative configurations of components of the closed-system grinding syringe of FIG. 1 or FIG. 5, in accordance with an application of the present invention.
Figure 7B:
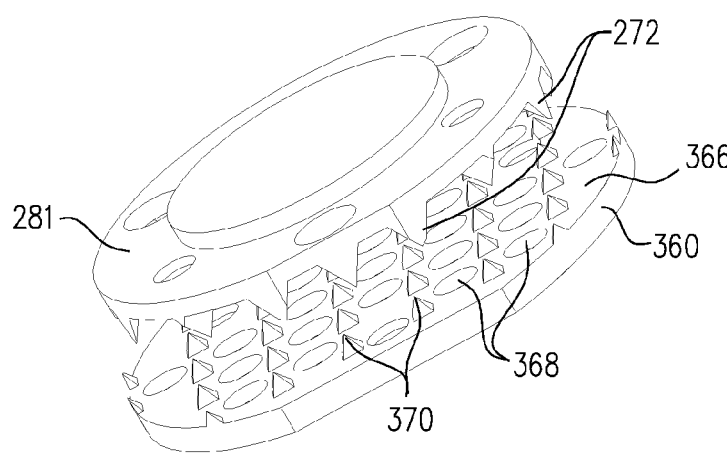
Figure 7C:
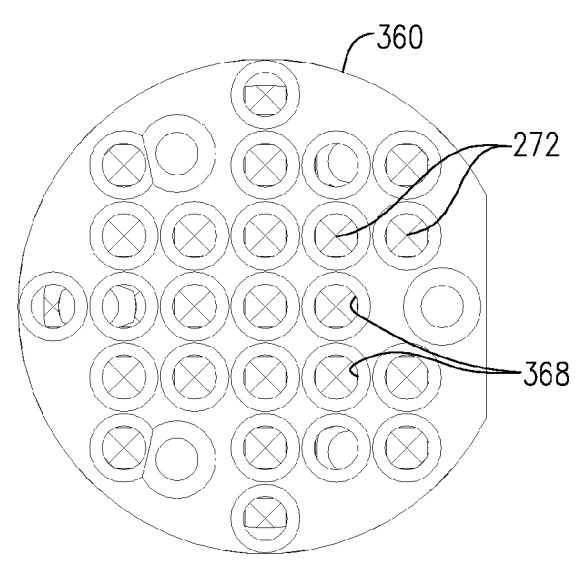
Figure 8A:
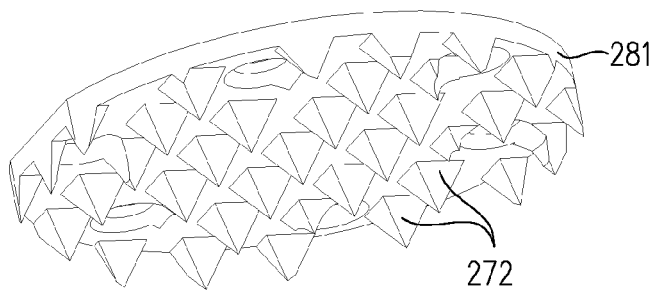
FIGS. 8A and 8B are schematic illustrations of a protrusion support and a solid-dosage-form support disc of the components of FIGS. 7A-C, in accordance with respective applications of the present invention.
Figure 8B:
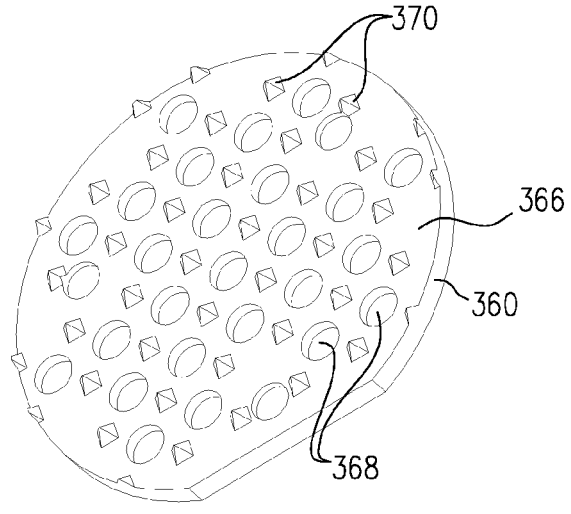

Reference is now made to FIGS. 7A-C, which are schematic illustrations of alternative configurations of components of closed-system grinding syringe 10 or 110, in accordance with an application of the present invention. Reference is also made to FIGS. 8A and 8B, which are schematic illustrations of a protrusion support 281 and a solid-dosage-form support disc 360, in accordance with respective applications of the present invention.

In these configurations, protrusion support 281 is provided that is shaped so as to define grinding protrusions 272, and to couple grinding protrusions 272 to plunger head 36, such that protrusion support 281 defines at least a portion of lower surface 40 of bottom plunger wall 38. In these configurations, protrusion support 281 replaces protrusion support 81, described hereinabove with reference to FIGS. 2A-B and 3. In these configurations, closed-system grinding syringe 10 comprises solid-dosage-form support disc 360, instead of solid-dosage-form support disc 60. Solid-dosage-form support disc 360 is shaped so as to define a plurality of holes 368 through solid-dosage-form support disc 360. Holes 368 are aligned with respective grinding protrusions 272, such that grinding protrusions 272 at least partially enter respective holes 368 when solid-dosage-form support disc 360 moves closer to lower surface 40 of bottom plunger wall 38 (and thus closer to grinding protrusions 272). This alignment can perhaps be best seen in FIG. 7C, which is a bottom-view of support disc 360, in which grinding protrusions 272 can be seen partially inserted into respective holes 368. This alignment allows solid-dosage-form support disc 360 to move close to protrusion support 281 (and lower surface 40 of bottom plunger wall 38), thereby increasing the strength of grinding of solid dosage form 20. For some applications, holes 368 have a diameter of at least 0.2 mm, no more than 0.6 mm, and/or between 0.2 and 0.6 mm, such as 0.4 mm.

Alternatively or additionally, for some applications, an upper surface 366 of solid-dosage-form support disc 360 is shaped so as to define support-disc grinding protrusions 370, which are not aligned with (i.e., do not overlap with) grinding protrusions 272, such that the two sets of grinding protrusions are interspersed with each other and increase the strength of grinding of solid dosage form 20. Alternatively, solid-dosage-form support disc 360 is not shaped so as to define any grinding protrusions.

Typically, closed-system grinding syringe 10 is configured such that upper surface 366 of solid-dosage-form support disc 360 (including support-disc grinding protrusions 370, if provided) and lower surface 40 of bottom plunger wall 38 (grinding protrusions 272) (lower surface 40 is defined at least in part by the lower surface of protrusion support 281) can come very close to each other, typically touch each other, if not blocked by remnants of solid dosage form 20 that fail to pass through holes 368.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus comprising a closed-system grinding syringe for liquefying and delivering a solid dosage form, the closed-system grinding syringe comprising:
   a barrel, which is shaped so as to define (a) a lateral wall shaped so as to define a cylindrical inner surface, (b) a top barrel opening, and (c) a bottom barrel wall;
   a fluid port disposed on the bottom barrel wall;
   a plunger, which comprises (a) a plunger shaft; (b) a plunger head shaped so as to define a bottom plunger wall shaped so as to define a lower surface; and (c) a plunger- head annular seal, wherein the plunger head is insertable into and moveable within the barrel such that (a) a portion of the barrel defines a closed-system syringe chamber between the bottom barrel wall and the lower surface of the bottom plunger wall, and (b) the plunger-head annular seal forms a plunger-head fluid-tight seal between an outer surface of the plunger head and the cylindrical inner surface of the barrel;
   a barrel cap, which is (a) configured to be attachable to the top barrel opening so as to form a barrel-cap fluid-tight seal with the top barrel opening, and (b) shaped so as to define a cap opening through the barrel cap, wherein the plunger shaft is slidably disposed through the cap opening so as to form a plunger-shaft fluid-tight seal between the plunger shaft and a perimeter of the cap opening;
   a solid-dosage-form support disc, which (a) is disposed below the bottom plunger wall so as to define a grinding compartment between the lower surface of the bottom plunger wall and an upper surface of the solid-dosage-form support disc, and (b) is shaped so as to define a plurality of holes through the solid-dosage-form support disc; and
   a knob,
   wherein the closed-system grinding syringe is configured such that when (a) the solid dosage form is disposed in the grinding compartment, (b) the plunger head is inserted into the barrel, and (c) the closed-system grinding syringe is oriented upright, upon activation of the knob, the grinding compartment grinds the solid dosage form to a powder and at least 75% of the powder passes through the plurality of holes into a portion of the closed-system syringe chamber below the solid-dosage-form support disc,
   wherein the closed-system grinding syringe is configured to move the lower surface of the bottom plunger wall and the upper surface of the solid-dosage-form support disc closer to each other as the grinding compartment grinds the solid dosage form, and
   wherein the closed-system grinding syringe is configured such that the lower surface of the bottom plunger wall does not rotate while the lower surface of the bottom plunger wall and the upper surface of the solid-dosage-form support disc move closer to each other as the grinding compartment grinds the solid dosage form.

2. The apparatus according to claim 1, wherein the closed-system grinding syringe is non-electrical and is configured such that when (a) the solid dosage form is disposed in the grinding compartment, (b) the plunger head is inserted into the barrel, and (c) the closed-system grinding syringe is oriented upright, upon mechanical activation of the knob, the grinding compartment grinds the solid dosage form.

3. The apparatus according to claim 1, wherein the closed-system grinding syringe is configured such that the knob is activated by rotation thereof.

4. The apparatus according to claim 1, wherein the barrel cap is fixed to the plunger such that the plunger shaft is slidably disposed through the cap opening and the plunger is not separable from the barrel cap during the normal use of the closed-system grinding syringe.

5. The apparatus according to claim 1, wherein the closed-system grinding syringe is shaped so as to define a liquid channel having (a) a first liquid-channel opening in fluid communication with the fluid port and (b) a second liquid-channel opening in fluid communication with the closed-system syringe chamber.

6. The apparatus according to claim 1, wherein the closed-system grinding syringe is shaped so as to define:
   a liquid channel having (a) a first liquid-channel opening in fluid communication with the fluid port and (b) a second liquid-channel opening in fluid communication with the closed-system syringe chamber, and
   a gas channel having a first gas-channel opening in fluid communication with the fluid port.

7. The apparatus according to claim 1, wherein the grinding compartment is shaped so as to define one or more lateral openings for insertion of the solid dosage form into the grinding compartment.

8. The apparatus according to claim 1, wherein the fluid port is configured to mate with a tip of a syringe.

9. The apparatus according to claim 1, wherein the fluid port is configured to mate with a feeding tube.

10. The apparatus according to claim 1,
   wherein the closed-system grinding syringe is configured to form a mixture of the powder and a liquid introduced into the closed-system syringe chamber via the fluid port, and
   wherein the closed-system grinding syringe is configured such that downward movement of the plunger head within the barrel delivers the mixture via the fluid port.

11. The apparatus according to claim 10,
   wherein the knob is coupled to the plunger shaft, and
   wherein the knob, the plunger shaft, and the barrel cap are arranged such that downward motion of the knob slides the plunger shaft downward through the cap opening of the barrel cap, thereby moving the plunger head downward within the barrel.

12. An apparatus comprising a closed-system grinding syringe for liquefying and delivering a solid dosage form, the closed-system grinding syringe comprising:

a barrel, which is shaped so as to define (a) a lateral wall shaped so as to define a cylindrical inner surface, (b) a top barrel opening, and (c) a bottom barrel wall;

a fluid port disposed on the bottom barrel wall;

a plunger, which comprises (a) a plunger shaft; (b) a plunger head shaped so as to define a bottom plunger wall shaped so as to define a lower surface; and (c) a plunger-head annular seal, wherein the plunger head is insertable into and moveable within the barrel such that (a) a portion of the barrel defines a closed-system syringe chamber between the bottom barrel wall and the lower surface of the bottom plunger wall, and (b) the plunger-head annular seal forms a plunger-head fluid-tight seal between an outer surface of the plunger head and the cylindrical inner surface of the barrel;

a barrel cap, which is (a) configured to be attachable to the top barrel opening so as to form a barrel-cap fluid-tight seal with the top barrel opening, and (b) shaped so as to define a cap opening through the barrel cap, wherein the plunger shaft is slidably disposed through the cap opening so as to form a plunger-shaft fluid-tight seal between the plunger shaft and a perimeter of the cap opening;

a solid-dosage-form support disc, which (a) is disposed below the bottom plunger wall so as to define a grinding compartment between the lower surface of the bottom plunger wall and an upper surface of the solid-dosage-form support disc, and (b) is shaped so as to define a plurality of holes through the solid-dosage-form support disc; and a knob, wherein the closed-system grinding syringe is configured such that when (a) the solid dosage form is disposed in the grinding compartment, (b) the plunger head is inserted into the barrel, and (c) the closed-system grinding syringe is oriented upright, upon activation of the knob, the grinding compartment grinds the solid dosage form to a powder and at least 75% of the powder passes through the plurality of holes into a portion of the closed-system syringe chamber below the solid-dosage-form support disc, wherein the lower surface of the bottom plunger wall is shaped so as to define grinding protrusions, and wherein the holes of the solid-dosage-form support disc are aligned with the grinding protrusions, such that the grinding protrusions at least partially enter respective holes when the solid-dosage-form support disc moves closer to the lower surface of the bottom plunger wall.

13. The apparatus according to claim 12, wherein the closed-system grinding syringe is configured to move the lower surface of the bottom plunger wall and the upper surface of the solid-dosage-form support disc closer to each other as the grinding compartment grinds the solid dosage form.

14. An apparatus comprising a closed-system grinding syringe for liquefying and delivering a solid dosage form, the closed-system grinding syringe comprising:

a barrel, which is shaped so as to define (a) a lateral wall shaped so as to define a cylindrical inner surface, (b) a top barrel opening, and (c) a bottom barrel wall;

a fluid port disposed on the bottom barrel wall;

a plunger, which comprises (a) a plunger shaft: (b) a plunger head shaped so as to define a bottom plunger wall shaped so as to define a lower surface; and (c) a plunger-head annular seal, wherein the plunger head is insertable into and moveable within the barrel such that (a) a portion of the barrel defines a closed-system syringe chamber between the bottom barrel wall and the lower surface of the bottom plunger wall, and (b) the plunger-head annular seal forms a plunger-head fluid-tight seal between an outer surface of the plunger head and the cylindrical inner surface of the barrel;

a barrel cap, which is (a) configured to be attachable to the top barrel opening so as to form a barrel-cap fluid-tight seal with the top barrel opening, and (b) shaped so as to define a cap opening through the barrel cap, wherein the plunger shaft is slidably disposed through the cap opening so as to form a plunger-shaft fluid-tight seal between the plunger shaft and a perimeter of the cap opening;

a solid-dosage-form support disc, which (a) is disposed below the bottom plunger wall so as to define a grinding compartment between the lower surface of the bottom plunger wall and an upper surface of the solid-dosage-form support disc, and (b) is shaped so as to define a plurality of holes through the solid-dosage-form support disc; and a knob, wherein the closed-system grinding syringe is configured such that when (a) the solid dosage form is disposed in the grinding compartment, (b) the plunger head is inserted into the barrel, and (c) the closed-system grinding syringe is oriented upright, upon activation of the knob, the grinding compartment grinds the solid dosage form to a powder and at least 75% of the powder passes through the plurality of holes into a portion of the closed-system syringe chamber below the solid-dosage-form support disc, wherein the lower surface of the bottom plunger wall is shaped so as to define grinding protrusions, wherein the grinding protrusions are bottom-plunger-wall grinding protrusions, and wherein the upper surface of the solid-dosage-form support disc is shaped so as to define support-disc grinding protrusions, which are not aligned with the bottom-plunger-wall grinding protrusions.

15. An apparatus comprising a closed-system grinding syringe for liquefying and delivering a solid dosage form, the closed-system grinding syringe comprising:

a barrel, which is shaped so as to define (a) a lateral wall shaped so as to define a cylindrical inner surface, (b) a top barrel opening, and (c) a bottom barrel wall;

a fluid port disposed on the bottom barrel wall;

a plunger, which comprises (a) a plunger shaft; (b) a plunger head shaped so as to define a bottom plunger wall shaped so as to define a lower surface; and (c) a plunger-head annular seal, wherein the plunger head is insertable into and moveable within the barrel such that (a) a portion of the barrel defines a closed-system syringe chamber between the bottom barrel wall and the lower surface of the bottom plunger wall, and (b) the plunger-head annular seal forms a plunger-head fluid-tight seal between an outer surface of the plunger head and the cylindrical inner surface of the barrel;

a barrel cap, which is (a) configured to be attachable to the top barrel opening so as to form a barrel-cap fluid-tight seal with the top barrel opening, and (b) shaped so as to define a cap opening through the barrel cap, wherein the plunger shaft is slidably disposed through the cap opening so as to form a plunger-shaft fluid-tight seal between the plunger shaft and a perimeter of the cap opening;

a solid-dosage-form support disc, which (a) is disposed below the bottom plunger wall so as to define a grinding compartment between the lower surface of the bottom plunger wall and an upper surface of the solid-dosage-form support disc, and (b) is shaped so as to define a plurality of holes through the solid-dosage-form support disc; and a knob, wherein the closed-system grinding syringe is configured such that when (a) the solid dosage form is disposed in the grinding compartment, (b) the plunger head is inserted into the barrel, and (c) the closed-system grinding syringe is oriented upright, upon activation of the knob, the grinding compartment grinds the solid dosage form to a powder and at least 75% of the powder passes through the plurality of holes into a portion of the closed-system syringe chamber below the solid-dosage-form support disc, wherein the closed-system grinding syringe is configured to move the lower surface of the bottom plunger wall and the upper surface of the solid-dosage-form support disc closer to each other as the grinding compartment grinds the solid dosage form, and wherein the closed-system grinding syringe is configured to move the upper surface of the solid-dosage-form support disc with respect to the cylindrical inner surface of the barrel as the grinding compartment grinds the solid dosage form.

16. The apparatus according to claim 15, wherein the closed-system grinding syringe is configured such that the upper surface of the solid-dosage-form support disc does not rotate during upward movement of the dosage-form support disc with respect to the cylindrical inner surface of the barrel.

17. The apparatus according to claim 15, wherein the closed-system grinding syringe further comprises:

an axially-moveable shaft, which (a) is disposed partially within the plunger shaft, (b) forms an axially-moveable shaft fluid-tight seal with an inner surface of the plunger shaft, (c) is connected to the solid-dosage-form support disc, (d) is rotationally-fixed with respect to the plunger shaft, and (e) is shaped so as to define an inner space having an internally-threaded wall; and an externally-threaded stem, which is (a) disposed partially within the plunger shaft, (b) axially fixed with respect to the plunger shaft, and (c) connected to the knob, and wherein an external thread of the externally-threaded stem is mated with an internal thread of the internally-threaded wall, such that rotation of the externally-threaded stem in one rotational direction causes upward axial movement of the axially-moveable shaft with respect to the plunger shaft, which in turn moves the upper surface of the solid-dosage-form support disc upward with respect to the cylindrical inner surface of the barrel, causing the grinding compartment to grind the solid dosage form.

18. An apparatus comprising a closed-system grinding syringe for liquefying and delivering a solid dosage form, the closed-system grinding syringe comprising:

a barrel, which is shaped so as to define (a) a lateral wall shaped so as to define a cylindrical inner surface, (b) a top barrel opening, and (c) a bottom barrel wall;

a fluid port disposed on the bottom barrel wall;

a plunger, which comprises (a) a plunger shaft: (b) a plunger head shaped so as to define a bottom plunger wall shaped so as to define a lower surface; and (c) a plunger-head annular seal, wherein the plunger head is insertable into and moveable within the barrel such that (a) a portion of the barrel defines a closed-system syringe chamber between the bottom barrel wall and the lower surface of the bottom plunger wall, and (b) the plunger-head annular seal forms a plunger-head fluid-tight seal between an outer surface of the plunger head and the cylindrical inner surface of the barrel;

a barrel cap, which is (a) configured to be attachable to the top barrel opening so as to form a barrel-cap fluid-tight seal with the top barrel opening, and (b) shaped so as to define a cap opening through the barrel cap, wherein the plunger shaft is slidably disposed through the cap opening so as to form a plunger-shaft fluid-tight seal between the plunger shaft and a perimeter of the cap opening:

a solid-dosage-form support disc, which (a) is disposed below the bottom plunger wall so as to define a grinding compartment between the lower surface of the bottom plunger wall and an upper surface of the solid-dosage-form support disc, and (b) is shaped so as to define a plurality of holes through the solid-dosage-form support disc; and a knob, wherein the closed-system grinding syringe is configured such that when (a) the solid dosage form is disposed in the grinding compartment, (b) the plunger head is inserted into the barrel, and (c) the closed-system grinding syringe is oriented upright, upon activation of the knob, the grinding compartment grinds the solid dosage form to a powder and at least 75% of the powder passes through the plurality of holes into a portion of the closed-system syringe chamber below the solid-dosage-form support disc, wherein the closed-system grinding syringe is shaped so as to define:

a liquid channel having (a) a first liquid-channel opening in fluid communication with the fluid port and (b) a second liquid-channel opening in fluid communication with the closed-system syringe chamber, and a gas channel having a first gas-channel opening in fluid communication with the fluid port, wherein the barrel is shaped so as to define an upper compartment between the barrel cap and the bottom plunger wall, when the barrel cap is attached to the top barrel opening, wherein the upper compartment is fluid-isolated from the closed-system syringe chamber and the external environment, wherein the liquid channel has a second liquid-channel opening in fluid communication with the closed-system syringe chamber through the bottom barrel wall, and wherein the gas channel has a second gas-channel opening in fluid communication with the upper compartment.

19. A method of liquefying and delivering a solid dosage form, the method comprising:

providing a closed-system grinding syringe including:

a barrel, which is shaped so as to define (a) a lateral wall shaped so as to define a cylindrical inner surface, (b) a top barrel opening, and (c) a bottom barrel wall;

a fluid port disposed on the bottom barrel wall;

a plunger, which includes (a) a plunger shaft; (b) a plunger head shaped so as to define a bottom plunger wall shaped so as to define a lower surface; and (c) a plunger-head annular seal;

a barrel cap, which is shaped so as to define a cap opening through the barrel cap, wherein the plunger shaft is slidably disposed through the cap opening so as to form a plunger-shaft fluid-tight seal between the plunger shaft and a perimeter of the cap opening;

a solid-dosage-form support disc, which (a) is disposed below the bottom plunger wall so as to define a grinding compartment between the lower surface of the bottom plunger wall and an upper surface of the solid-dosage-form support disc, and (b) is shaped so as to define a plurality of holes through the solid-dosage-form support disc; and a knob;

inserting the solid dosage form into the grinding compartment;

thereafter, inserting the plunger head into the barrel such that (a) a portion of the barrel defines a closed-system syringe chamber between the bottom barrel wall and the lower surface of the bottom plunger wall, (b) the plunger-head annular seal forms a plunger-head fluid-tight seal between an outer surface of the plunger head and the cylindrical inner surface of the barrel;

thereafter, attaching the barrel cap to the top barrel opening so as to form a barrel-cap fluid-tight seal with the top barrel opening;

thereafter, while the closed-system grinding syringe is oriented upright, activating the knob such that the grinding compartment grinds the solid dosage form to a powder and at least 75% of the powder passes through the plurality of holes into a portion of the closed-system syringe chamber below the solid-dosage-form support disc;

thereafter, introducing a liquid into the closed-system syringe chamber via the fluid port;

thereafter, mixing the powder with the liquid to form a mixture; and thereafter, delivering the mixture via the fluid port by moving the plunger head downward within the barrel, wherein the closed-system grinding syringe is configured to move the lower surface of the bottom plunger wall and the upper surface of the solid-dosage-form support disc closer to each other as the grinding compartment grinds the solid dosage form, and wherein the closed-system grinding syringe is configured such that the lower surface of the bottom plunger wall does not rotate while the lower surface of the bottom plunger wall and the upper surface of the solid-dosage-form support disc move closer to each other as the grinding compartment grinds the solid dosage form.

20. The method according to claim 19, wherein introducing the liquid into the closed-system syringe chamber via the fluid port comprising coupling a syringe to the fluid port and injecting the liquid from the syringe into the closed-system syringe chamber via the fluid port.

21. The method according to claim 19, wherein delivering the mixture comprises coupling the fluid port to a feeding tube and delivering the mixture to the feeding tube.

22. The method according to claim 19, wherein the knob is coupled to the plunger shaft, and wherein delivering the mixture via the fluid port by moving the plunger head downward within the barrel comprises moving the knob downward so as to slide the plunger shaft downward through the cap opening of the barrel cap.

23. The method according to claim 19, wherein the closed-system grinding syringe is configured to move the upper surface of the solid-dosage-form support disc with respect to the cylindrical inner surface of the barrel as the grinding compartment grinds the solid dosage form.

* * * * *